(12) United States Patent
Wiedenheft et al.

(10) Patent No.: US 10,087,431 B2
(45) Date of Patent: Oct. 2, 2018

(54) METHODS OF GENERATING NUCLEIC ACID FRAGMENTS

(75) Inventors: Blake Wiedenheft, Oakland, CA (US); Kaihong Zhou, Moraga, CA (US); Jennifer A. Doudna, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 676 days.

(21) Appl. No.: 13/039,160

(22) Filed: Mar. 2, 2011

(65) Prior Publication Data

US 2011/0223638 A1    Sep. 15, 2011

Related U.S. Application Data

(60) Provisional application No. 61/312,510, filed on Mar. 10, 2010.

(51) Int. Cl.
*A61K 38/46* (2006.01)
*C12N 9/22* (2006.01)
*C12P 19/34* (2006.01)

(52) U.S. Cl.
CPC .............. *C12N 9/22* (2013.01); *A61K 38/465* (2013.01); *C12P 19/34* (2013.01)

(58) Field of Classification Search
None
See application file for complete search history.

(56) References Cited

U.S. PATENT DOCUMENTS 6,524,578 B1 *   2/2003   Tackett .................. 424/94.1

OTHER PUBLICATIONS

G.V. Tetz et al., "Effect of DNase and Antibiotics on Biofilm Characteristics", Antimicrobial Agents and Chemotherapy 53(3):1204-1209 (Dec. 2008).*
Makarova et al., "A DNA repair system specific for thermophilic Archaea and bacteria predicted by genomic context analysis", *Nucleic Acids Res*, 30:482-496 (2002).
Makarova et al., "A putative RNA-interference-based immune system in prokaryotes: computational analysis of the predicted enzymatic machinery, functional analogies with eukaryotic RNAi, and hypothetical mechanisms of action", *Biology Direct*, 1:1-26 (2006).
Wiedenheft et al., "Structural Basis for DNase Activity of a Conserved Protein Implicated in CRISPR-Mediated Genome Defense", *Structure*, 17:904-912 (2009).

* cited by examiner

*Primary Examiner* — Rebecca E Prouty
(74) *Attorney, Agent, or Firm* — Bozicevic Field & Francis, LLP; Paula A. Borden; Kyle A. Gurley

(57) ABSTRACT

Provided herein are methods of using a Cas1 polypeptide to generate nucleic fragments from a DNA substrate. These methods may be performed in vitro or in vivo. Also provided are methods of screening for modulators of Cas1.

12 Claims, 15 Drawing Sheets

Specification includes a Sequence Listing.

```
DvCas1_2781520_CASS1   1 MKKL............L.NTLYVTTQG.......TYLAKEGECIVV.RVGDE.......VRLRVPV
CtCas1_1006874_CASS1   1 MKKH............L.NTLFVTTQG.......SYLSKEGECVLI.SIDRV.......EKTRIPL
SpCas1_901811_CASS1    1 MKKL............L.NTLYLTQED.......FYVTKEGDNIVI.KQEGK.......VLKRFPF
EcCas1_947228_CASS2    1 MTWLP...........LNPIP.LKDRVSMIFLQYGQIDVIDGAFVLIDKTG........IRTHIPV
TtCas1_3169280_CASS2   1 MPPVSSA.......RN.LKELPKFRDGLSYLYVEHAVVEREAGGIGIYDQEG.......L.TLAPV
CdCas1_2650014_CASS2   1 MPYSHDAIAFSTIPASHQIR.LEDRLSFLYLEYCLIRQDRTGVIAIQNGHNESSDEEEKLEPQILRIQLPV
YpCas1_1175302_CASS3   1 MAMENAIH..SSD.LKTIL.HSKRSNIYYLEYCRVLVNGGRVEYVTDEGK.......QSLYWNIPI
EcCas1_3993120_CASS3   1 MSSN.YLT..PSD.LKTIL.HSKRANIYYLEKCRVQVNGGRVEYVTSEGK.......ESYYWNIPI
PaCas1_4380485_CASS3   1 MDD...IS..PSE.LKTIL.HSKRANLYYLQHCRVLVNGGRVEYVTDEGR.......HSHYWNIPI
NmCas1_906625_CASS4    1 ..............GKLSLQRRQLLI.QQNGE........SH.TVPL
StCas1_3165126_CASS4   1 ..............MTWRSLLIQNG.......EKMRLKLDNLLV.QKMGQ........EF.TVPL
CjCas1_905808_CASS4    1 ..............MTWRVHVSQS.......AKLNLELNHLVI.KQDEN........IA.KLFL
SsCas1_1454460_CASS5   1 MSYD..........EAFKTLLISSN.......AYVYVKKNMLVI.KKGDK........KVEISP
ApCas1_1445886_CASS5   1 MIS...........VRTIVISEYG.......SRIRVARGALVV.ETKAG........KKV.VVE
AfCas1_1485099_CASS5   1 ..............MMMVVAEPG.......KYLGIENGLIVV.KEKGK........ALRKVRP
NeCas1_4274010_CASS6   1 ..............MRLIVVDGFG.......VVLELESGAIVF.RENGE........RIGTVPI
MtCas1_888506_CASS6    1 ..............M.TSLFVDRRG.......SRISFADGRVIV.WSEEL........GESQYPI
TtCas1_3169526_CASS6   1 ..............M.VQLYVSDSV.......ATLRLRQGRLLL.EEEGR........EVAGFPA
TtCas1_997745_CASS7    1 MQ............MTIHLTRQG.......FANGKLYRKDNTICV.EGEK........EKKYFPV
TmCas1_897836_CASS7    1 M.............KTLYL..........FSSGTLKRKANTICL.ETES........GRKYIPV
AaCas1_1193018_CASS7   1 MG............ESVYL..........NSHGTLSRHENTLRF.ENAE........VKKDIPV
consensus>50             ..........................................................
```

FIG. 9A

```
DvCas1_2781520_CASS1  39  HSLGGVVC.FGQVSCSPFLMGFAAERGLGFSFLTEHGRFLARVQGPVSG..............NVLLRREQYRR
CtCas1_1006874_CASS1  39  HMLNGIVC.FGQVSCSPFLIGHCAQLGVAVTFLTEHGRFLCQMQGPVKG..............NILLRRAQYRM
SpCas1_901811_CASS1   39  RIIDGIVC.FSYLGVSSALVKLCTENQINLSFHTPQGRFCGRYIGSTNG..............NVLLRREHYRL
EcCas1_947228_CASS2   47  GSVACIML.EPGTRVSHAAVRLAAQVGTLLVWGEAGVRVYASGQPG..............G..ARSDKLLYQAKL
TtCas1_3169280_CASS2  51  AGLGVLFL.GPGTRITHAAVRLLAENGCTVAWVGEGMARFYAQGLGD..............T..RSAARFYRQARA
CdCas1_2650014_CASS2  71  ASLAVLCL.GPGTSISNAAMTSCTRSGCTVIFTGGGVNAYSHATPL..............T..STAKWAIAQACL
YpCas1_1175302_CASS3  56  ANTTVIML.GTGTSVTQAAMREFARAGVLVGFCGGGGTPLFAANDVEVNVSWLTAQSEYRPTEYLHDWVSF
EcCas1_3993120_CASS3  55  ANTTALIL.GMGTSVTQAAMREFAHAGVMVGFCGTDGTPLYSANEVDVDVSWLSPQSEYRPTEYLQQWVSF
PaCas1_4380485_CASS3  53  ANTTSLLL.GTGTSITQAAMRELARAGVLVGFCGGGGTPLFSANEVDVEVSWLTPQSEYRPTEYLQRWVGF
NmCas1_906625_CASS4   35  EDIAVIIENRETLITAPLLSALAEHGATLLTCDEQFLPCGQWLPYAQY..............HRQLKILKLQL
StCas1_3165126_CASS4  35  SDISIIVAEGGDTVVTILRLLSALSKYNIALVVCDNEHLPTGIYHSQNGH..............FRAYKRLKEQL
CjCas1_905808_CASS4   39  KDINIIVLESLQISISSALFNAFAKYKIILLTCDETHSINGVFTPFLGH..............FQSAKIAKEQM
SsCas1_1454460_CASS5  37  SEVDEILIT.VSCSISTSALSLALTHGISVMFLNSRETPWGILLPSIVT..............ETVKTKKAQYE
ApCas1_1445886_CASS5  33  SSVERVIISSSRVSISSAAVRAAAKMGIDLVFLDWDGSPVARLYPPIIN..............KTVATRIGQFS
AfCas1_1485099_CASS5  34  EDLKQVLII.GKAAISSDAIKLLLKNRVDVVFLDFNGEILGRLSHPLIG..............TAKTRREQYL
NeCas1_4274010_CASS6  35  APLTRVFL.RGDVKLPAALIGKLGEQGVGVVILSGRIGRPSLLLARPHN..............DAARRVVQIRL
MtCas1_888506_CASS6   35  ETLDGITL.FGRPTMTTPFIVEMLKRERDIQLFTTDGHYQGRISTPDVS..............YAPRLRQQVHR
TtCas1_3169526_CASS6  34  RQVRSVAL.WGNVRLSTPALVFLLRQGVPVFFYSLEGFLHGVAGAYPDP..............HPAHLRAQFA.
TtCas1_997745_CASS7   34  ESVRDIYV.FGEVDLNKKFIEFAEEKEIILHFFGYYGNYVGSFYPRE..............HYNSGYIILKQAEHY
TmCas1_897836_CASS7   33  ENVMDIKV.FGEVDLNKRFLEFLSQKRIPIHFFNREGYYVGTFYPRE..............YLNSGFLILKQAEHY
AaCas1_1193018_CASS7  34  EDVEEIFV.FAELSLNTKLLNFLASKGIPLHFFNYYGYTGTFYPRE..............SSVSGHLLIKQVEHY
consensus>50
```

FIG. 9B

```
DvCas1_2781520_CASS1   98  ADSPEASAEVARSIVSAKVVNARGVLQRAMRDHGDKVD...GVALEAEVIHLRAC......LMRLQQPAGL
CtCas1_1006874_CASS1   98  ADNYDQTATLARLFVIGKIGNARVTLARALRDHPEKTD...GEKLKNAQHVLAGC......IRRLQEATDQ
SpCas1_901811_CASS1    98  SDR.EESLEYAKRFILAKISNSRKYLLRFKRDHRQQID...TKLFEAVNDELIWA......LEMVQAADNK
EcCas1_947228_CASS2   106  ALDEDLRLKVVRKMFELRFGEPAPA................................................RRSV
TtCas1_3169280_CASS2  110  WADPALHLEVVMRLYRMRFSEPLPE................................................GLTL
CdCas1_2650014_CASS2  130  VSNTEYQKKAALAFYKRQFGGNAIT................................................GGSI
YpCas1_1175302_CASS3  126  WFDDEKRLAAAVAFQRIRIAQIQQHWLSSHIQRESLFP.VNHDQLLFIL...TRF......EQNLANCLTS
EcCas1_3993120_CASS3  125  WFVEDKRLAAAKRFQLIRLTHIDKHWSSSKMLREHAFQ.PDVNALHTLL...NRT......CEEIDAAENH
PaCas1_4380485_CASS3  123  WFDEEKRLVAARHFQRARLERIRHSWLEDRVLRDAGFA.VDATALAVAV..EDS......ARALEQAPNH
NmCas1_906625_CASS4    95  NISEPLKKQLWQHIVRQKILNQAFVADETGNDLA.A...KRLRTLASEV....................RS
StCas1_3165126_CASS4   95  DWSQKQKEKAWQIVTYYKINNQEDVLAMFEKSLDNI....RLLSDYKEQI....................EP
CjCas1_905808_CASS4    99  NVSAQKKAILWQKIKNKILNQAFILKKHNKIEQ.S.....NELINLAKKV....................SL
SsCas1_1454460_CASS5   96  AIVVRKDNRYGEEIISSKIYNQSVHLKYWARVTGT.....KN........D...................YK
ApCas1_1445886_CASS5   93  A.NERLRRLIAAELVSAKIYNQGQTLKYIARQRAD.....ERLREAGYEVELLSGEPLRIADEDGPGFR
AfCas1_1485099_CASS5   92  AYGDKRGVHLAKEFIKAKMANQMAILTNLAKARKDSNPEV.AESLLKAKKEIDACLNELDGVEAEMIDKVR
NeCas1_4274010_CASS6   94  SFDKPFCLQIAKALIERKLTRQIEWFAELRENDMQ....V.RYELSHALRALEEH......RSRIGHVSSA
MtCas1_888506_CASS6    94  TDDPAFCLSLSKRIVSRKILNQQALIRAHTSGQ.........DVAESIRTMKHS......LAWVDRSGSL
TtCas1_3169526_CASS6   92  ....AEGIPLARAFVVGKIRSALALLERHRLPEA......GG......VVEA......LARAEGASEL
TtCas1_997745_CASS7    95  L.DSARRLDLARRFVQGAVANMTQVLKYYQNRGRDLE...DY.LHAI..SAL......EASLLSVSSI
TmCas1_897836_CASS7    94  I.NQEKRMLIAREIVSRSFQNMVDFLKKRKVRADSLT...RY........................KKKAEEASNV
AaCas1_1193018_CASS7   95  L.DAQ..KRLYLAKSFVIGSILNLEYVYK....ISAD...TY........................LNKVKETNSI
consensus>50
```

FIG. 9C

```
DvCas1_2781520_CASS1  160  DAVRGIEGEAAKGYFSVFDNLLITREAAFRFEGR........SRRPPLDRVNCLLSFIYTLLGHDVRSALEGV
CtCas1_1006874_CASS1  160  ELIRGIEGEAAKAYFSVFDECITADDPAFRFEGR........SRRPPLDRVNCLLSFVYTLMTHDIRSALESC
SpCas1_901811_CASS1   159  DSLRGIEGQAANQYFRIFNDLVLTDKKTFYFQGR........SKRPPLDCVNALLSFGYSLLTFECQSALEAV
EcCas1_947228_CASS2   135  EQLRGIEGSRVRATYALLAKQYG..VTWNGR..R..YD.PKDWEKGDTINQCISAATSCLYGVTEAAILAA
TtCas1_3169280_CASS2  139  EQVRGLEGVRVRNAYARWSRETG..VPWYGR..S..YD.RGNWRAADPVNRALSAGASYLYGLAHAAIVSL
CdCas1_2650014_CASS2  159  SVMRGLEGRIMRNTYRENAKKAG..IRGFKR..D.....T...KAADPVNVGLNISNSILYGAAATVCTAI
YpCas1_1175302_CASS3  187  NDLMVQEAVLTKALYKLAANTVN..YGDFTR..A..K.R..GGGIDLANRFLDHGNYLAYGLAATATWVI
EcCas1_3993120_CASS3  186  TQLMLVEAKLTKALYKMVSQTVG..YGDFTR..A..K.R..GGGIDMANRFLDQGNYLAYGLAAVAAWT
PaCas1_4380485_CASS3  184  EHLLTEEARLSKRLFKLAAQATR..YGEFVR..A..K.R..GSGGDPANRFLDHGNYLAYGLAATATWVL
NmCas1_906625_CASS4   142  GDTGNREAQAAALYFQAL.............FGEK.FT.RN...DNNAVNAALNYTYAVLRAAVARALTLY
StCas1_3165126_CASS4  143  GDRTNREGHAAKVYFNEL.............FGKQ.FV.RVTQQEADVINAGLNYGYAIMRAQMARIVAGY
CjCas1_905808_CASS4   146  NDSKNIEAVAAALYFKTL.............FGTS.FS.RD...ELCFENSALNYGYAIIRACIIRAVCIS
SsCas1_1454460_CASS5  136  ELLDKDEPAAARVYWQNISQLLP..KDIGFDGR........D.VDGTDQFNMALNYSYAILYNTIFKYLVIA
ApCas1_1445886_CASS5  158  DKLLSIEARASRRYWQCIAEILP..GRLGFSGR........D.RGALDPFNAALNYGYGMLYSIVEKSLLLV
AfCas1_1485099_CASS5  162  ERLIGIEGKASKHYWDAISIVIP..EEYRFNGRGIEIGSPRYAKDIVNAMLNYGYSILLAECVKAVELA
NeCas1_4274010_CASS6  154  ASLRGVEGSAAARYFSGLQAVVP..DSLHFSGR........NRRPPRDPFNALLSLTYTLLHSEIAIALYGT
MtCas1_888506_CASS6   149  AELNGFEGNAAKAYFTALGHLVP..QEFAFQGR........STRPPLDAFNSMVSLGYSLLYKNIIGAIERH
ErCas1_3169526_CASS6  138  ERLRGAEGEGSRVYFQGLARLL..GPYGFGGR........TRRPPRDPVNAALSYGYALLLGRVLVAVRLA
EeCas1_997745_CASS7   150  EELMALEGNIRRYYESFNTILD..DTPFVL..........KN.RNKRPPTDPLNALISFGNSLVYTKILTEIYKT
TmCas1_897836_CASS7   142  SELMGIEGNAREEYYSMIDSLVS..DERFRI..........EK.RTRRPPKNFANTLISFGNSLLYTTVLSLIYQT
AaCas1_1193018_CASS7  137  PELMSVEAEFRKLCYKKLEEVTG..WEL.............EK.RTKRPPQNPLNALISFGNSLTYAKVLGEIYKT
consensus>50               .........................E.........................D..N.............
```

FIG. 9D

```
DvCas1_2781520_CASS1   225  GLDSAVGFLHRDRPGRHGLALDVMEEFRAVVADRLALSLINLGK.LKKSDFE.IQETGAVRMTDDARKALL
CtCas1_1006874_CASS1   225  GLDPAAGFLHKDRPGRPSLALDMLEEFRSYIGDRIVLSLINRGQ.IHAKDFD.ISETGAVAMKDDARKTLI
SpCas1_901811_CASS1    224  GLDSYVGFFHTDRPGRASLALDLVEEFRSYIVDRFVFSLINKGQ.LQKKHFE.VKENGSILLTENGRAIFI
EcCas1_947228_CASS2    199  GYAPAIGFVHTG..KPLSFVYDIADIIKFDTVVPKAFEIARRNP.GEPD....REVRLACRDIFRSSKTL
TtCas1_3169280_CASS2   203  GFSPALGFIHTG..KLLSFVYDIADLYKADYLVPAAFRTVAESE.EAVE....RRVRRALREAIQEGRLL
CdCas1_2650014_CASS2   218  GVNPALGIIHRGD..TRSLIFDLADLYKASIVIPIVFSHAKDED...PV....TNIRRHLRREIHSRKIM
YpCas1_1175302_CASS3   248  GLPHGLSVLHGKT.RRGGLVFDVADLIKDALVLPQAFIAAMQGE..EE.....QEFRQRCISGFQRTEAL
EcCas1_3993120_CASS3   247  GIPHGLAVMHGKT.RRGGLVFDLADLIKDALVMPQAFIAAMAGE...DA....QEFRQRCVNIFQQADAL
PaCas1_4380485_CASS3   245  GIPHGLAVLHGKT.RRGGLVFDVADLIKDSLILPQAFLSAMRGD..EE.....QDFRQACLDNLSRAQAL
NmCas1_906625_CASS4    195  GWLPALGLFHRSELNPFNLADDFIEPLRPLADLTVIHLYE.QGR.LKTELTL.GIK........QHLI
StCas1_3165126_CASS4   199  GLNGLLGIFHKNEYNQFNLVDDLMEPFRQIVDVWYDNLR.DQEFLKYEYRL.G...........LT
CjCas1_905808_CASS4    199  GLLPWLGIKHDNIYNSFALCDDLIEVFRASVDDCVLKLKG.ESEFLSKDDKR.A...........LI
SsCas1_1454460_CASS5   197  GLDPYLGFIHKDRPGNESLIVYDFSEMFKPYIDFLLVRALRSGF.RLKVK........G.GLIEENSRGDLA
ApCas1_1445886_CASS5   217  GLDPYLGVFHSEKSGKPSLTLDAIEPFRAPIVDRIL.ALKAGRMYLKLE........A.GRLDYKSRKEVA
AfCas1_1485099_CASS5   230  GLDPYAGFLHVDVSGRSSIAIDLMENFRQQVVDRVVLRLISYRQ.IKPEDCE..KRNMVCQLSDNARRLLL
NeCas1_4274010_CASS6   216  GFDPYVGFYHRLAFGRESLASDLLEPLR.PLADQFALALIRKKV.LEKDHFS..TTEAGCLLGKAGRTRYY
MtCas1_888506_CASS6    211  SLNAYIGFLHQDSRGHATLASDLMEVWRAPIIDDTVLRLIADGV.VDTRAFSKNSDTGAVFATREATRSIA
GlHPEVGFLHAEGRRSPALALDLMEEFRVPVVDQVVLSAFRRGL.LTPSHAE.VRE.GGVYLNEEGRRRLI
TtCas1_3169526_CASS6   199  GLHPEVGFLHAEGRRSPALALDLMEEFRVPVVDQVVLSAFRRGL.LTPSHAE.VRE.GGVYLNEEGRRRLI
TtCas1_997745_CASS7    213  HLDPRIGYLHTTNFRRFTLNLDVAEIFKPIYADRVLFTLLKKNI.IKEDDFE..TQGEISLLKERGRRLYV
TmCas1_897836_CASS7    205  HLDPRIGYLHETNFRRFSLNLDIAELFKPAVVDRLFTNLVNTRQ.INEKHFD..EISEGLMLNDEGKSLFV
AaCas1_1193018_CASS7   197  QLNPTVSYLHEPSTKRFSLSLDVAEVFKPIFVDNLIIRLIQENK.IDKTHFS..TELNMTFLNEIGRKVFL
consensus>50                .............H........L..D..E.............................
```

FIG. 9E

```
DvCas1_2781520_CASS1  294  VAYQKRKQDEIV.HPELNERIPLGLVFHVQAMLMA.......RWLRGDLD.GYPP..........F.VWK
CtCas1_1006874_CASS1  294  TAYQQRKQEEIE.HPFVGEKMAVGLLWHMQAMLLA.......RYIRGDID.MYPP..........F.VWR
SpCas1_901811_CASS1   293  DLWQKRKHTEVE.HPFTKEKVKLMLLPYVQAQLLA.......KAIRGDLE.SYPP..........F.M.V
EcCas1_947228_CASS2   262  AKLIPLIEDVLA..AGEIQPPAP..PEDAQPVAIPLPVSLG.................DA..GHRSS
TtCas1_3169280_CASS2  266  ERMAEDLLNLFR..GIGLPEEED..PVEEDPTRPGGLWDLEGEVEGGVAYGGDDP.GEGA..EEPEG
CdCas1_2650014_CASS2  279  AGMLEALMEVLT..PYLPNRNDD..RLIGDSDEVK........GHIQYGKEI........N
YpCas1_1175302_CASS3  310  DVMIDGIKETAA..LCSQVP.......................................R
EcCas1_3993120_CASS3  309  DVMITSLQETAQ..ALAKAD.......................................Q
PaCas1_4380485_CASS3  307  DFMIDTLKDVAQ..RSTVS........................................A
NmCas1_906625_CASS4   252  KILYYQTSIER.........QHFSTLAAIDKMISSFQ.........AGVTDKNA.KQLKLPEILPLKEYQYE
StCas1_3165126_CASS4  253  DLLNAKIKYGK.........ETCSVTVAMDKYVKGFI.........KYISEKDS.SKFHCPVVSSLE..WRK
CjCas1_905808_CASS4   253  GNLQSKINFDG.........QNYPLNRAINHYVANFK.........NALLYEDE.LKIVK.........FDD
SsCas1_1454460_CASS5  258  KLIRKGMEENVK.EESDHNPKTLIQAIRAHAVKLA.........SSIREGKE.YRGFK.........LVM
ApCas1_1445886_CASS5  278  KAVASSLSMKAA.VRGLGRRIRLEDAIMVQARWLA.........EAFRGSGG.FSAVR.........LGL
AfCas1_1485099_CASS5  298  ASLLERLDSKTQ..YRGRNLAYSSIILLHARDVV.........AELRGERR.YEGFV.........QKW
NeCas1_4274010_CASS6  283  AAYGEHS..ETL.RKGINQEIEWLTAQVNEILATA.........ED....DVQ.PDDS..FEDFG
MtCas1_888506_CASS6   281  RAFGNRIARTATYIKGDPHRYTFQYALDLQLSIV.........RVIEAGHP.SRLVDIDITS..EPSGA
TtCas1_3169526_CASS6  267  QLFEERLLEGVS.HP.LGFRKPLGETIEVQAQRLK.........AALLGRGR.YTPF.........Y.LWR
TtCas1_997745_CASS7   281  QEFEGKLQTTFY.HRRLKRNVSYQTLMRLELYKLE.........KHLIGEEL.YEPFV.........SRW
TmCas1_897836_CASS7   273  KNYEQALRETVF.HKKLNRYVSMRSLIKMELHKLE.........KHLIGEQV.FGSE.........E
AaCas1_1193018_CASS7  265  KAFNELLETTIF.YPKLNRKVSHRTLIKLELYKLI.........KHLLEEEV.YLPLN.........YGGLK
consensus>50
```

FIG. 9F

```
  1 mddispselk tilhskranl yylqhcrvlv nggrveyvtd egrhshywni pianttslll
 61 gtgtsitqaa mrelaragvl vgfcggggtp lfsanevdve vswltpqsey rpteylqrwv
121 gfwfdeekrl vaarhfqrar lerirhswle drvlrdagfa vdatalavav edsaralega
181 pnhehlltee arlskrlfkl aaqatrygef vrakrgsggd panrfldhgn ylayglaata
241 twvlgiphgl avlhgktrrg glvfdvadli kdslilpqaf lsamrgdeeq dfrqacldnl
301 sraqaldfmi dtlkdvaqrs tvsa
```

FIG. 10

SEQUENCE LISTING

```
<160> NUMBER OF SEQ ID NOS: 24

<210> SEQ ID NO 1
<211> LENGTH: 343
<212> TYPE: PRT
<213> ORGANISM: Desulfovibrio vulgaris

<400> SEQUENCE: 1

Met Lys Lys Leu Leu Asn Thr Leu Tyr Val Thr Thr Gln Gly Thr Tyr
1               5                   10                  15

Leu Ala Lys Glu Gly Glu Cys Ile Val Val Arg Val Gly Asp Glu Val
            20                  25                  30

Arg Leu Arg Val Pro Val His Ser Leu Gly Gly Val Val Cys Phe Gly
        35                  40                  45

Gln Val Ser Cys Ser Pro Phe Leu Met Gly Phe Ala Ala Glu Arg Gly
    50                  55                  60

Leu Gly Phe Ser Phe Leu Thr Glu His Gly Arg Phe Leu Ala Arg Val
65                  70                  75                  80

Gln Gly Pro Val Ser Gly Asn Val Leu Leu Arg Arg Glu Gln Tyr Arg
                85                  90                  95

Arg Ala Asp Ser Pro Glu Ala Ser Ala Glu Val Ala Arg Ser Ile Val
            100                 105                 110

Ser Ala Lys Val Val Asn Ala Arg Gly Val Leu Gln Arg Ala Met Arg
        115                 120                 125
```

```
Asp His Gly Asp Lys Val Asp Gly Val Ala Leu Glu Ala Glu Val Leu
130                 135                 140

His Leu Arg Ala Cys Leu Met Arg Leu Gln Gln Pro Ala Gly Leu Asp
145                 150                 155                 160

Ala Val Arg Gly Ile Glu Gly Glu Ala Ala Lys Gly Tyr Phe Ser Val
                165                 170                 175

Phe Asp Asn Leu Ile Leu Thr Arg Glu Ala Ala Phe Arg Phe Glu Gly
                180                 185                 190

Arg Ser Arg Arg Pro Pro Leu Asp Arg Val Asn Cys Leu Leu Ser Phe
        195                 200                 205

Ile Tyr Thr Leu Leu Gly His Asp Val Arg Ser Ala Leu Glu Gly Val
        210                 215                 220

Gly Leu Asp Ser Ala Val Gly Phe Leu His Arg Asp Arg Pro Gly Arg
225                 230                 235                 240

His Gly Leu Ala Leu Asp Val Met Glu Glu Phe Arg Ala Val Val Ala
                245                 250                 255

Asp Arg Leu Ala Leu Ser Leu Ile Asn Leu Gly Lys Leu Lys Lys Ser
                260                 265                 270

Asp Phe Glu Ile Gln Glu Thr Gly Ala Val Arg Met Thr Asp Asp Ala
                275                 280                 285

Arg Lys Ala Leu Leu Val Ala Tyr Gln Lys Arg Lys Gln Asp Glu Ile
        290                 295                 300

Val His Pro Phe Leu Asn Glu Arg Ile Pro Leu Gly Leu Val Phe His
305                 310                 315                 320

Val Gln Ala Met Leu Met Ala Arg Trp Leu Arg Gly Asp Leu Asp Gly
                325                 330                 335

Tyr Pro Pro Phe Val Trp Lys
                340

<210> SEQ ID NO 2
<211> LENGTH: 343
<212> TYPE: PRT
<213> ORGANISM: Chlorobium tepidum

<400> SEQUENCE: 2

Met Lys Lys His Leu Asn Thr Leu Phe Val Thr Thr Gln Gly Ser Tyr
1               5                   10                  15

Leu Ser Lys Glu Gly Glu Cys Val Leu Ile Ser Ile Asp Arg Val Glu
                20                  25                  30

Lys Thr Arg Ile Pro Leu His Met Leu Asn Gly Ile Val Cys Phe Gly
            35                  40                  45

Gln Val Ser Cys Ser Pro Phe Leu Leu Gly His Cys Ala Gln Leu Gly
        50                  55                  60

Val Ala Val Thr Phe Leu Thr Glu His Gly Arg Phe Leu Cys Gln Met
65                  70                  75                  80

Gln Gly Pro Val Lys Gly Asn Ile Leu Leu Arg Arg Ala Gln Tyr Arg
                85                  90                  95

Met Ala Asp Asn Tyr Asp Gln Thr Ala Thr Leu Ala Arg Leu Phe Val
                100                 105                 110

Ile Gly Lys Ile Gly Asn Ala Arg Val Thr Leu Ala Arg Ala Leu Arg
            115                 120                 125

Asp His Pro Glu Lys Thr Asp Gly Glu Lys Leu Lys Asn Ala Gln His
        130                 135                 140

Val Leu Ala Gly Cys Ile Arg Arg Leu Gln Glu Ala Thr Asp Gln Glu
```

```
                145                 150                 155                 160
        Leu Ile Arg Gly Ile Glu Gly Glu Ala Ala Lys Ala Tyr Phe Ser Val
                        165                 170                 175

Phe Asp Glu Cys Ile Thr Ala Asp Pro Ala Phe Arg Phe Glu Gly
                        180                 185                 190

Arg Ser Arg Arg Pro Pro Leu Asp Arg Val Asn Cys Leu Leu Ser Phe
                        195                 200                 205

Val Tyr Thr Leu Met Thr His Asp Ile Arg Ser Ala Leu Glu Ser Cys
                210                 215                 220

Gly Leu Asp Pro Ala Ala Gly Phe Leu His Lys Asp Arg Pro Gly Arg
        225                 230                 235                 240

Pro Ser Leu Ala Leu Asp Met Leu Glu Glu Phe Arg Ser Tyr Ile Gly
                        245                 250                 255

Asp Arg Leu Val Leu Ser Leu Ile Asn Arg Gly Gln Ile His Ala Lys
                        260                 265                 270

Asp Phe Asp Ile Ser Glu Thr Gly Ala Val Ala Met Lys Asp Asp Ala
                        275                 280                 285

Arg Lys Thr Leu Ile Thr Ala Tyr Gln Gln Arg Lys Gln Glu Glu Ile
                290                 295                 300

Glu His Pro Phe Val Gly Glu Lys Met Ala Val Gly Leu Leu Trp His
        305                 310                 315                 320

Met Gln Ala Met Leu Leu Ala Arg Tyr Ile Arg Gly Asp Ile Asp Met
                        325                 330                 335

Tyr Pro Pro Phe Val Trp Arg
                        340

<210> SEQ ID NO 3
<211> LENGTH: 341
<212> TYPE: PRT
<213> ORGANISM: Streptococcus pyogenes

<400> SEQUENCE: 3

Met Lys Lys Leu Leu Asn Thr Leu Tyr Leu Thr Gln Glu Asp Phe Tyr
        1               5                   10                  15

Val Thr Lys Glu Gly Asp Asn Ile Val Ile Lys Gln Glu Gly Lys Val
                        20                  25                  30

Leu Lys Arg Phe Pro Phe Arg Ile Ile Asp Gly Ile Val Cys Phe Ser
                        35                  40                  45

Tyr Leu Gly Val Ser Ser Ala Leu Val Lys Leu Cys Thr Glu Asn Gln
                50                  55                  60

Ile Asn Leu Ser Phe His Thr Pro Gln Gly Arg Phe Cys Gly Arg Tyr
        65                  70                  75                  80

Ile Gly Ser Thr Asn Gly Asn Val Leu Leu Arg Arg Glu His Tyr Arg
                        85                  90                  95

Leu Ser Asp Arg Glu Glu Ser Leu Glu Tyr Ala Lys Arg Phe Ile Leu
                        100                 105                 110

Ala Lys Ile Ser Asn Ser Arg Lys Tyr Leu Leu Arg Phe Lys Arg Asp
                        115                 120                 125

His Arg Gln Gln Ile Asp Thr Lys Leu Phe Glu Ala Val Asn Asp Glu
                130                 135                 140

Leu Ile Trp Ala Leu Glu Met Val Gln Ala Ala Asp Asn Lys Asp Ser
        145                 150                 155                 160

Leu Arg Gly Ile Glu Gly Gln Ala Ala Asn Gln Tyr Phe Arg Ile Phe
                        165                 170                 175
```

-continued

Asn Asp Leu Val Leu Thr Asp Lys Lys Thr Phe Tyr Phe Gln Gly Arg
                180                 185                 190

Ser Lys Arg Pro Pro Leu Asp Cys Val Asn Ala Leu Leu Ser Phe Gly
        195                 200                 205

Tyr Ser Leu Leu Thr Phe Glu Cys Gln Ser Ala Leu Glu Ala Val Gly
    210                 215                 220

Leu Asp Ser Tyr Val Gly Phe Phe His Thr Asp Arg Pro Gly Arg Ala
225                 230                 235                 240

Ser Leu Ala Leu Asp Leu Val Glu Glu Phe Arg Ser Tyr Ile Val Asp
                245                 250                 255

Arg Phe Val Phe Ser Leu Ile Asn Lys Gly Gln Leu Gln Lys Lys His
            260                 265                 270

Phe Glu Val Lys Glu Asn Gly Ser Ile Leu Leu Thr Glu Asn Gly Arg
        275                 280                 285

Ala Ile Phe Ile Asp Leu Trp Gln Lys Arg Lys His Thr Glu Val Glu
    290                 295                 300

His Pro Phe Thr Lys Glu Lys Val Lys Leu Met Leu Leu Pro Tyr Val
305                 310                 315                 320

Gln Ala Gln Leu Leu Ala Lys Ala Ile Arg Gly Asp Leu Glu Ser Tyr
                325                 330                 335

Pro Pro Phe Met Val
            340

<210> SEQ ID NO 4
<211> LENGTH: 305
<212> TYPE: PRT
<213> ORGANISM: Escherichia coli

<400> SEQUENCE: 4

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
        195                 200                 205

Thr Gly Lys Pro Leu Ser Phe Val Tyr Asp Ile Ala Asp Ile Ile Lys
            210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
            245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Pro Glu Asp Ala Gln Pro
        275                 280                 285

Val Ala Ile Pro Leu Pro Val Ser Leu Gly Asp Ala Gly His Arg Ser
290                 295                 300

Ser
305

<210> SEQ ID NO 5
<211> LENGTH: 325
<212> TYPE: PRT
<213> ORGANISM: Thermus thermophilus

<400> SEQUENCE: 5

Met Pro Pro Val Ser Ser Ala Arg Asn Leu Lys Glu Leu Pro Lys Phe
1               5                   10                  15

Arg Asp Gly Leu Ser Tyr Leu Tyr Val Glu His Ala Val Val Glu Arg
            20                  25                  30

Glu Ala Gly Gly Ile Gly Ile Tyr Asp Gln Glu Gly Leu Thr Leu Ala
        35                  40                  45

Pro Val Ala Gly Leu Gly Val Leu Phe Leu Gly Pro Gly Thr Arg Ile
    50                  55                  60

Thr His Ala Ala Val Arg Leu Leu Ala Glu Asn Gly Cys Thr Val Ala
65                  70                  75                  80

Trp Val Gly Glu Gly Met Ala Arg Phe Tyr Ala Gln Gly Leu Gly Asp
                85                  90                  95

Thr Arg Ser Ala Ala Arg Phe Tyr Arg Gln Ala Arg Ala Trp Ala Asp
            100                 105                 110

Pro Ala Leu His Leu Glu Val Val Met Arg Leu Tyr Arg Met Arg Phe
        115                 120                 125

Ser Glu Pro Leu Pro Glu Gly Leu Thr Leu Glu Gln Val Arg Gly Leu
130                 135                 140

Glu Gly Val Arg Val Arg Asn Ala Tyr Ala Arg Trp Ser Arg Glu Thr
145                 150                 155                 160

Gly Val Pro Trp Tyr Gly Arg Ser Tyr Asp Arg Gly Asn Trp Arg Ala
            165                 170                 175

Ala Asp Pro Val Asn Arg Ala Leu Ser Ala Gly Ala Ser Tyr Leu Tyr
        180                 185                 190

Gly Leu Ala His Ala Ala Ile Val Ser Leu Gly Phe Ser Pro Ala Leu
    195                 200                 205

Gly Phe Ile His Thr Gly Lys Leu Leu Ser Phe Val Tyr Asp Ile Ala
210                 215                 220

Asp Leu Tyr Lys Ala Asp Tyr Leu Val Pro Ala Ala Phe Arg Thr Val
225                 230                 235                 240

Ala Glu Ser Glu Glu Ala Val Glu Arg Val Arg Arg Ala Leu Arg
            245                 250                 255

Glu Ala Ile Gln Glu Gly Arg Leu Leu Glu Arg Met Ala Glu Asp Leu

```
            260                 265                 270

Leu Asn Leu Phe Arg Gly Leu Gly Leu Pro Glu Glu Glu Asp Pro Val
        275                 280                 285

Glu Glu Asp Pro Thr Arg Pro Gly Gly Leu Trp Asp Leu Glu Gly Glu
    290                 295                 300

Val Glu Gly Gly Val Ala Tyr Gly Gly Asp Asp Pro Gly Glu Gly Ala
305                 310                 315                 320

Glu Glu Pro Glu Gly
                325

<210> SEQ ID NO 6
<211> LENGTH: 319
<212> TYPE: PRT
<213> ORGANISM: Corynebacterium diphtheriae

<400> SEQUENCE: 6

Met Pro Tyr Ser His Asp Ala Ile Ala Phe Ser Thr Ile Pro Ala Ser
 1               5                  10                  15

His Gln Ile Arg Leu Glu Asp Arg Leu Ser Phe Leu Tyr Leu Glu Tyr
            20                  25                  30

Cys Leu Ile Arg Gln Asp Arg Thr Gly Val Ile Ala Ile Gln Asn Gly
        35                  40                  45

His Asn Glu Ser Ser Asp Glu Glu Glu Lys Leu Glu Pro Gln Ile Leu
    50                  55                  60

Arg Ile Gln Leu Pro Val Ala Ser Leu Ala Val Leu Cys Leu Gly Pro
65                  70                  75                  80

Gly Thr Ser Ile Ser Asn Ala Ala Met Thr Ser Cys Thr Arg Ser Gly
                85                  90                  95

Cys Thr Val Ile Phe Thr Gly Gly Gly Gly Val Asn Ala Tyr Ser His
            100                 105                 110

Ala Thr Pro Leu Thr Ser Thr Ala Lys Trp Ala Ile Ala Gln Ala Cys
        115                 120                 125

Leu Val Ser Asn Thr Glu Tyr Gln Lys Lys Ala Ala Leu Ala Phe Tyr
    130                 135                 140

Lys Arg Gln Phe Gly Gly Asn Ala Ile Thr Gly Gly Ser Ile Ser Val
145                 150                 155                 160

Met Arg Gly Leu Glu Gly Arg Ile Met Arg Asn Thr Tyr Arg Glu Asn
                165                 170                 175

Ala Lys Lys Ala Gly Ile Arg Gly Phe Lys Arg Asp Thr Lys Ala Ala
            180                 185                 190

Asp Pro Val Asn Val Gly Leu Asn Ile Ser Asn Ser Ile Leu Tyr Gly
        195                 200                 205

Ala Ala Ala Thr Val Cys Thr Ala Ile Gly Val Asn Pro Ala Leu Gly
    210                 215                 220

Ile Ile His Arg Gly Asp Thr Arg Ser Leu Leu Phe Asp Leu Ala Asp
225                 230                 235                 240

Leu Tyr Lys Ala Ser Ile Val Ile Pro Leu Val Phe Ser His Ala Lys
                245                 250                 255

Asp Glu Asp Pro Val Thr Asn Ile Arg Arg His Leu Arg Arg Glu Ile
            260                 265                 270

His Ser Arg Lys Ile Met Ala Gly Met Leu Glu Ala Leu Met Glu Val
        275                 280                 285

Leu Thr Pro Tyr Leu Pro Asn Arg Asn Asp Asp Arg Leu Ile Gly Asp
    290                 295                 300
```

-continued

```
Ser Asp Glu Val Lys Gly His Ile Gln Tyr Gly Lys Glu Ile Asn
305                 310                 315
```

<210> SEQ ID NO 7
<211> LENGTH: 328
<212> TYPE: PRT
<213> ORGANISM: Yersinia pestis

<400> SEQUENCE: 7

```
Met Ala Met Glu Asn Ala Ile His Ser Ser Asp Leu Lys Thr Ile Leu
 1               5                  10                  15

His Ser Lys Arg Ser Asn Ile Tyr Tyr Leu Glu Tyr Cys Arg Val Leu
            20                  25                  30

Val Asn Gly Gly Arg Val Glu Tyr Val Thr Asp Glu Gly Lys Gln Ser
        35                  40                  45

Leu Tyr Trp Asn Ile Pro Ile Ala Asn Thr Thr Val Ile Met Leu Gly
    50                  55                  60

Thr Gly Thr Ser Val Thr Gln Ala Ala Met Arg Glu Phe Ala Arg Ala
65                  70                  75                  80

Gly Val Leu Val Gly Phe Cys Gly Gly Gly Gly Thr Pro Leu Phe Ala
                85                  90                  95

Ala Asn Asp Val Glu Val Asn Val Ser Trp Leu Thr Ala Gln Ser Glu
            100                 105                 110

Tyr Arg Pro Thr Glu Tyr Leu His Asp Trp Val Ser Phe Trp Phe Asp
        115                 120                 125

Asp Glu Lys Arg Leu Ala Ala Ala Val Ala Phe Gln Arg Ile Arg Ile
    130                 135                 140

Ala Gln Ile Gln Gln His Trp Leu Ser Ser His Ile Gln Arg Glu Ser
145                 150                 155                 160

Leu Phe Pro Val Asn His Asp Gln Leu Leu Phe Ile Leu Thr Arg Phe
                165                 170                 175

Glu Gln Asn Leu Ala Asn Cys Leu Thr Ser Asn Asp Leu Met Val Gln
            180                 185                 190

Glu Ala Val Leu Thr Lys Ala Leu Tyr Lys Leu Ala Ala Asn Thr Val
        195                 200                 205

Asn Tyr Gly Asp Phe Thr Arg Ala Lys Arg Gly Gly Gly Ile Asp Leu
    210                 215                 220

Ala Asn Arg Phe Leu Asp His Gly Asn Tyr Leu Ala Tyr Gly Leu Ala
225                 230                 235                 240

Ala Thr Ala Thr Trp Val Ile Gly Leu Pro His Gly Leu Ser Val Leu
                245                 250                 255

His Gly Lys Thr Arg Arg Gly Gly Leu Val Phe Asp Val Ala Asp Leu
            260                 265                 270

Ile Lys Asp Ala Leu Val Leu Pro Gln Ala Phe Ile Ala Ala Met Gln
        275                 280                 285

Gly Glu Glu Glu Gln Glu Phe Arg Gln Arg Cys Ile Ser Gly Phe Gln
    290                 295                 300

Arg Thr Glu Ala Leu Asp Val Met Ile Asp Gly Ile Lys Glu Thr Ala
305                 310                 315                 320

Ala Leu Cys Ser Gln Val Pro Arg
                325
```

<210> SEQ ID NO 8
<211> LENGTH: 327
<212> TYPE: PRT
<213> ORGANISM: Escherichia coli

<400> SEQUENCE: 8

Met Ser Ser Asn Tyr Leu Thr Pro Ser Asp Leu Lys Thr Ile Leu His
1               5                   10                  15

Ser Lys Arg Ala Asn Ile Tyr Tyr Leu Glu Lys Cys Arg Val Gln Val
            20                  25                  30

Asn Gly Gly Arg Val Glu Tyr Val Thr Ser Glu Gly Lys Glu Ser Tyr
        35                  40                  45

Tyr Trp Asn Ile Pro Ile Ala Asn Thr Thr Ala Leu Ile Leu Gly Met
    50                  55                  60

Gly Thr Ser Val Thr Gln Ala Ala Met Arg Glu Phe Ala His Ala Gly
65                  70                  75                  80

Val Met Val Gly Phe Cys Gly Thr Asp Gly Thr Pro Leu Tyr Ser Ala
                85                  90                  95

Asn Glu Val Asp Val Asp Val Ser Trp Leu Ser Pro Gln Ser Glu Tyr
            100                 105                 110

Arg Pro Thr Glu Tyr Leu Gln Gln Trp Val Ser Phe Trp Phe Val Glu
        115                 120                 125

Asp Lys Arg Leu Ala Ala Lys Arg Phe Gln Leu Ile Arg Leu Thr
130                 135                 140

His Ile Asp Lys His Trp Ser Ser Lys Met Leu Arg Glu His Ala
145                 150                 155                 160

Phe Gln Pro Asp Val Asn Ala Leu His Thr Leu Leu Asn Arg Thr Cys
                165                 170                 175

Glu Glu Ile Asp Ala Ala Glu Asn His Thr Gln Leu Met Leu Val Glu
            180                 185                 190

Ala Lys Leu Thr Lys Ala Leu Tyr Lys Met Val Ser Gln Thr Val Gly
        195                 200                 205

Tyr Gly Asp Phe Thr Arg Ala Lys Arg Gly Gly Ile Asp Met Ala
210                 215                 220

Asn Arg Phe Leu Asp Gln Gly Asn Tyr Leu Ala Tyr Gly Leu Ala Ala
225                 230                 235                 240

Val Ala Ala Trp Val Thr Gly Ile Pro His Gly Leu Ala Val Met His
                245                 250                 255

Gly Lys Thr Arg Arg Gly Gly Leu Val Phe Asp Leu Ala Asp Leu Ile
            260                 265                 270

Lys Asp Ala Leu Val Met Pro Gln Ala Phe Ile Ala Ala Met Ala Gly
        275                 280                 285

Glu Asp Ala Gln Glu Phe Arg Gln Arg Cys Val Asn Ile Phe Gln Gln
    290                 295                 300

Ala Asp Ala Leu Asp Val Met Ile Thr Ser Leu Gln Glu Thr Ala Gln
305                 310                 315                 320

Ala Leu Ala Lys Ala Asp Gln
            325

<210> SEQ ID NO 9
<211> LENGTH: 324
<212> TYPE: PRT
<213> ORGANISM: Pseudomonas aeruginosa

<400> SEQUENCE: 9

Met Asp Asp Ile Ser Pro Ser Glu Leu Lys Thr Ile Leu His Ser Lys
1               5                   10                  15

Arg Ala Asn Leu Tyr Tyr Leu Gln His Cys Arg Val Leu Val Asn Gly
            20                  25                  30

```
Gly Arg Val Glu Tyr Val Thr Asp Glu Gly Arg His Ser His Tyr Trp
            35                  40                  45

Asn Ile Pro Ile Ala Asn Thr Thr Ser Leu Leu Gly Thr Gly Thr
        50                  55                  60

Ser Ile Thr Gln Ala Ala Met Arg Glu Leu Ala Arg Ala Gly Val Leu
 65                  70                  75                  80

Val Gly Phe Cys Gly Gly Gly Thr Pro Leu Phe Ser Ala Asn Glu
                85                  90                  95

Val Asp Val Glu Val Ser Trp Leu Thr Pro Gln Ser Glu Tyr Arg Pro
                100                 105                 110

Thr Glu Tyr Leu Gln Arg Trp Val Gly Phe Trp Phe Asp Glu Glu Lys
            115                 120                 125

Arg Leu Val Ala Ala Arg His Phe Gln Arg Ala Arg Leu Glu Arg Ile
            130                 135                 140

Arg His Ser Trp Leu Glu Asp Arg Val Leu Arg Asp Ala Gly Phe Ala
145                 150                 155                 160

Val Asp Ala Thr Ala Leu Ala Val Ala Val Glu Asp Ser Ala Arg Ala
                165                 170                 175

Leu Glu Gln Ala Pro Asn His Glu His Leu Leu Thr Gly Glu Ala Arg
            180                 185                 190

Leu Ser Lys Arg Leu Phe Lys Leu Ala Ala Gln Ala Thr Arg Tyr Gly
            195                 200                 205

Glu Phe Val Arg Ala Lys Arg Gly Ser Gly Gly Asp Pro Ala Asn Arg
210                 215                 220

Phe Leu Asp His Gly Asn Tyr Leu Ala Tyr Gly Leu Ala Ala Thr Ala
225                 230                 235                 240

Thr Trp Val Leu Gly Ile Pro His Gly Leu Ala Val Leu His Gly Lys
                245                 250                 255

Thr Arg Arg Gly Gly Leu Val Phe Asp Val Ala Asp Leu Ile Lys Asp
            260                 265                 270

Ser Leu Ile Leu Pro Gln Ala Phe Leu Ser Ala Met Arg Gly Asp Glu
            275                 280                 285

Glu Gln Asp Phe Arg Gln Ala Cys Leu Asp Asn Leu Ser Arg Ala Gln
            290                 295                 300

Ala Leu Asp Phe Met Ile Asp Thr Leu Lys Asp Val Ala Gln Arg Ser
305                 310                 315                 320

Thr Val Ser Ala

<210> SEQ ID NO 10
<211> LENGTH: 304
<212> TYPE: PRT
<213> ORGANISM: Neisseria meningitidis

<400> SEQUENCE: 10

Met Thr Trp Arg Ser Leu Leu Ile Gln Asn Gly Gly Lys Leu Ser Leu
  1               5                  10                  15

Gln Arg Arg Gln Leu Leu Ile Gln Gln Asn Gly Glu Ser His Thr Val
             20                  25                  30

Pro Leu Glu Asp Ile Ala Val Ile Ile Glu Asn Arg Glu Thr Leu
            35                  40                  45

Ile Thr Ala Pro Leu Leu Ser Ala Leu Ala Glu His Gly Ala Thr Leu
        50                  55                  60

Leu Thr Cys Asp Glu Gln Phe Leu Pro Cys Gly Gln Trp Leu Pro Tyr
 65                  70                  75                  80
```

```
Ala Gln Tyr His Arg Gln Leu Lys Ile Leu Lys Leu Gln Leu Asn Ile
                 85                  90                  95

Ser Glu Pro Leu Lys Lys Gln Leu Trp Gln His Ile Val Arg Gln Lys
            100                 105                 110

Ile Leu Asn Gln Ala Phe Val Ala Asp Glu Thr Gly Asn Asp Leu Ala
        115                 120                 125

Ala Lys Arg Leu Arg Thr Leu Ala Ser Glu Val Arg Ser Gly Asp Thr
    130                 135                 140

Gly Asn Arg Glu Ala Gln Ala Ala Ala Leu Tyr Phe Gln Ala Leu Phe
145                 150                 155                 160

Gly Glu Lys Phe Thr Arg Asn Asp Asn Ala Val Asn Ala Ala Leu
                165                 170                 175

Asn Tyr Thr Tyr Ala Val Leu Arg Ala Ala Val Ala Arg Ala Leu Thr
            180                 185                 190

Leu Tyr Gly Trp Leu Pro Ala Leu Gly Leu Phe His Arg Ser Glu Leu
        195                 200                 205

Asn Pro Phe Asn Leu Ala Asp Asp Phe Ile Glu Pro Leu Arg Pro Leu
    210                 215                 220

Ala Asp Leu Thr Val Ile His Leu Tyr Glu Gln Gly Arg Leu Lys Thr
225                 230                 235                 240

Glu Leu Thr Leu Gly Ile Lys Gln His Leu Ile Lys Ile Leu Tyr Tyr
                245                 250                 255

Gln Thr Ser Ile Glu Arg Gln His Phe Ser Thr Leu Ala Ala Ile Asp
            260                 265                 270

Lys Met Ile Ser Ser Phe Gln Ala Gly Val Thr Asp Lys Asn Ala Lys
        275                 280                 285

Gln Leu Lys Leu Pro Glu Ile Leu Pro Leu Lys Glu Tyr Gln Tyr Glu
    290                 295                 300

<210> SEQ ID NO 11
<211> LENGTH: 303
<212> TYPE: PRT
<213> ORGANISM: Streptococcus thermophilus

<400> SEQUENCE: 11

Met Thr Trp Arg Val Val His Val Ser Gln Ser Glu Lys Met Arg Leu
1               5                   10                  15

Lys Leu Asp Asn Leu Leu Val Gln Lys Met Gly Gln Glu Phe Thr Val
            20                  25                  30

Pro Leu Ser Asp Ile Ser Ile Ile Val Ala Glu Gly Gly Asp Thr Val
        35                  40                  45

Val Thr Leu Arg Leu Leu Ser Ala Leu Ser Lys Tyr Asn Ile Ala Leu
    50                  55                  60

Val Val Cys Asp Asn Glu His Leu Pro Thr Gly Ile Tyr His Ser Gln
65                  70                  75                  80

Asn Gly His Phe Arg Ala Tyr Lys Arg Leu Lys Glu Gln Leu Asp Trp
                85                  90                  95

Ser Gln Lys Gln Lys Glu Lys Ala Trp Gln Ile Val Thr Tyr Tyr Lys
            100                 105                 110

Ile Asn Asn Gln Glu Asp Val Leu Ala Met Phe Glu Lys Ser Leu Asp
        115                 120                 125

Asn Ile Arg Leu Leu Ser Asp Tyr Lys Glu Gln Ile Glu Pro Gly Asp
    130                 135                 140

Arg Thr Asn Arg Glu Gly His Ala Ala Lys Val Tyr Phe Asn Glu Leu
```

```
                145                 150                 155                 160
        Phe Gly Lys Gln Phe Val Arg Val Thr Gln Gln Glu Ala Asp Val Ile
                        165                 170                 175

Asn Ala Gly Leu Asn Tyr Gly Tyr Ala Ile Met Arg Ala Gln Met Ala
                        180                 185                 190

Arg Ile Val Ala Gly Tyr Gly Leu Asn Gly Leu Leu Gly Ile Phe His
                        195                 200                 205

Lys Asn Glu Tyr Asn Gln Phe Asn Leu Val Asp Asp Leu Met Glu Pro
                        210                 215                 220

Phe Arg Gln Ile Val Asp Val Trp Val Tyr Asp Asn Leu Arg Asp Gln
        225                 230                 235                 240

Glu Phe Leu Lys Tyr Glu Tyr Arg Leu Gly Leu Thr Asp Leu Leu Asn
                        245                 250                 255

Ala Lys Ile Lys Tyr Gly Lys Glu Thr Cys Ser Val Thr Val Ala Met
                        260                 265                 270

Asp Lys Tyr Val Lys Gly Phe Ile Lys Tyr Ile Ser Glu Lys Asp Ser
                        275                 280                 285

Ser Lys Phe His Cys Pro Val Val Ser Ser Leu Glu Trp Arg Lys
                        290                 295                 300

<210> SEQ ID NO 12
<211> LENGTH: 296
<212> TYPE: PRT
<213> ORGANISM: Campylobacter jejuni

<400> SEQUENCE: 12

Met Ser Tyr Asp Glu Ala Phe Lys Thr Leu Leu Ile Ser Ser Asn Ala
        1               5                   10                  15

Lys Leu Asn Leu Glu Leu Asn His Leu Val Ile Lys Gln Asp Glu Asn
                        20                  25                  30

Ile Ala Lys Leu Phe Leu Lys Asp Ile Asn Ile Val Leu Glu Ser
                        35                  40                  45

Leu Gln Ile Ser Ile Ser Ser Ala Leu Phe Asn Ala Phe Ala Lys Tyr
        50                  55                  60

Lys Ile Ile Leu Leu Thr Cys Asp Glu Thr His Ser Ile Asn Gly Val
        65                  70                  75                  80

Phe Thr Pro Phe Leu Gly His Phe Gln Ser Ala Lys Ile Ala Lys Glu
                        85                  90                  95

Gln Met Asn Val Ser Ala Gln Lys Lys Ala Ile Leu Trp Gln Lys Ile
                        100                 105                 110

Ile Lys Asn Lys Ile Leu Asn Gln Ala Phe Ile Leu Lys Lys His Asn
                        115                 120                 125

Lys Ile Glu Gln Ser Asn Glu Leu Ile Asn Leu Ala Lys Lys Val Ser
                        130                 135                 140

Leu Asn Asp Ser Lys Asn Ile Glu Ala Val Ala Ala Leu Tyr Phe
        145                 150                 155                 160

Lys Thr Leu Phe Gly Thr Ser Phe Ser Arg Asp Glu Leu Cys Phe Glu
                        165                 170                 175

Asn Ser Ala Leu Asn Tyr Gly Tyr Ala Ile Ile Arg Ala Cys Ile Ile
                        180                 185                 190

Arg Ala Val Cys Ile Ser Gly Leu Leu Pro Trp Leu Gly Ile Lys His
                        195                 200                 205

Asp Asn Ile Tyr Asn Ser Phe Ala Leu Cys Asp Asp Leu Ile Glu Val
                        210                 215                 220
```

```
Phe Arg Ala Ser Val Asp Asp Cys Val Leu Lys Leu Lys Gly Glu Ser
225                 230                 235                 240

Glu Phe Leu Ser Lys Asp Asp Lys Arg Ala Leu Ile Gly Asn Leu Gln
                245                 250                 255

Ser Lys Ile Asn Phe Asp Gly Gln Asn Tyr Pro Leu Asn Arg Ala Ile
            260                 265                 270

Asn His Tyr Val Ala Asn Phe Lys Asn Ala Leu Leu Tyr Glu Asp Glu
        275                 280                 285

Leu Lys Ile Val Lys Phe Asp Asp
        290                 295
```

<210> SEQ ID NO 13
<211> LENGTH: 307
<212> TYPE: PRT
<213> ORGANISM: Sulfolobus solfataricus

<400> SEQUENCE: 13

```
Met Ile Ser Val Arg Thr Leu Val Ile Ser Glu Tyr Gly Ala Tyr Val
1               5                   10                  15

Tyr Val Lys Lys Asn Met Leu Val Ile Lys Lys Gly Asp Lys Lys Val
                20                  25                  30

Glu Ile Ser Pro Ser Glu Val Asp Glu Ile Leu Ile Thr Val Ser Cys
            35                  40                  45

Ser Ile Ser Thr Ser Ala Leu Ser Leu Ala Leu Thr His Gly Ile Ser
        50                  55                  60

Val Met Phe Leu Asn Ser Arg Glu Thr Pro Trp Gly Ile Leu Leu Pro
65                  70                  75                  80

Ser Ile Val Thr Glu Thr Val Lys Thr Lys Lys Ala Gln Tyr Glu Ala
                85                  90                  95

Ile Val Val Arg Lys Asp Asn Arg Tyr Gly Glu Ile Ile Ser Ser
            100                 105                 110

Lys Ile Tyr Asn Gln Ser Val His Leu Lys Tyr Trp Ala Arg Val Thr
        115                 120                 125

Gly Thr Lys Asn Asp Tyr Lys Glu Leu Leu Asp Lys Asp Glu Pro Ala
130                 135                 140

Ala Ala Arg Val Tyr Trp Gln Asn Ile Ser Gln Leu Leu Pro Lys Asp
145                 150                 155                 160

Ile Gly Phe Asp Gly Arg Asp Val Asp Gly Thr Asp Gln Phe Asn Met
                165                 170                 175

Ala Leu Asn Tyr Ser Tyr Ala Ile Leu Tyr Asn Thr Ile Phe Lys Tyr
            180                 185                 190

Leu Val Ile Ala Gly Leu Asp Pro Tyr Leu Gly Phe Ile His Lys Asp
        195                 200                 205

Arg Pro Gly Asn Glu Ser Leu Val Tyr Asp Phe Ser Glu Met Phe Lys
    210                 215                 220

Pro Tyr Ile Asp Phe Leu Leu Val Arg Ala Leu Arg Ser Gly Phe Arg
225                 230                 235                 240

Leu Lys Val Lys Gly Leu Ile Glu Glu Asn Ser Arg Gly Asp Leu
                245                 250                 255

Ala Lys Leu Ile Arg Lys Gly Met Glu Glu Asn Val Lys Glu Glu Ser
            260                 265                 270

Asp His Asn Pro Lys Thr Leu Ile Gln Ala Ile Arg Ala His Ala Val
        275                 280                 285

Lys Leu Ala Ser Ser Ile Arg Glu Gly Lys Glu Tyr Arg Gly Phe Lys
    290                 295                 300
```

Leu Val Met
305

<210> SEQ ID NO 14
<211> LENGTH: 327
<212> TYPE: PRT
<213> ORGANISM: Aeropyrum pernix

<400> SEQUENCE: 14

Met Met Met Val Val Ala Glu Pro Gly Ser Arg Ile Arg Val Ala Arg
1               5                   10                  15

Gly Ala Leu Val Val Glu Thr Lys Ala Gly Lys Lys Val Val Glu
            20                  25                  30

Ser Ser Val Glu Arg Val Ile Ile Ser Ser Ser Arg Val Ser Ile Ser
        35                  40                  45

Ser Ala Ala Val Arg Ala Ala Ala Lys Met Gly Ile Asp Leu Val Phe
    50                  55                  60

Leu Asp Trp Asp Gly Ser Pro Val Ala Arg Leu Tyr Pro Pro Ile Ile
65                  70                  75                  80

Asn Lys Thr Val Ala Thr Arg Ile Gly Gln Phe Ser Ala Asn Glu Arg
                85                  90                  95

Leu Arg Arg Leu Ile Ala Ala Glu Leu Val Ser Ala Lys Ile Tyr Asn
            100                 105                 110

Gln Gly Gln Thr Leu Lys Tyr Ile Ala Arg Gln Arg Ala Asp Glu Arg
        115                 120                 125

Leu Arg Glu Ala Gly Tyr Glu Val Glu Leu Ser Gly Glu Pro Leu
    130                 135                 140

Arg Ile Ala Asp Glu Asp Gly Pro Gly Phe Arg Asp Lys Leu Leu Ser
145                 150                 155                 160

Ile Glu Ala Arg Ala Ser Arg Arg Tyr Trp Gln Cys Ile Ala Glu Ile
                165                 170                 175

Leu Pro Gly Arg Leu Gly Phe Ser Gly Arg Asp Arg Gly Ala Leu Asp
            180                 185                 190

Pro Phe Asn Ala Ala Leu Asn Tyr Gly Tyr Gly Met Leu Tyr Ser Ile
        195                 200                 205

Val Glu Lys Ser Leu Leu Leu Val Gly Leu Asp Pro Tyr Leu Gly Val
    210                 215                 220

Phe His Ser Glu Lys Ser Gly Lys Pro Ser Leu Thr Leu Asp Ala Ile
225                 230                 235                 240

Glu Pro Phe Arg Ala Pro Ile Val Asp Arg Ile Leu Ala Leu Lys Ala
                245                 250                 255

Gly Arg Met Tyr Leu Lys Leu Glu Ala Gly Arg Leu Asp Tyr Lys Ser
            260                 265                 270

Arg Lys Glu Val Ala Lys Ala Val Ala Ser Ser Leu Ser Met Lys Ala
        275                 280                 285

Ala Val Arg Gly Leu Gly Arg Arg Ile Arg Leu Glu Asp Ala Ile Met
    290                 295                 300

Val Gln Ala Arg Trp Leu Ala Glu Ala Phe Arg Gly Ser Gly Gly Phe
305                 310                 315                 320

Ser Ala Val Arg Leu Gly Leu
                325

<210> SEQ ID NO 15
<211> LENGTH: 345
<212> TYPE: PRT

<213> ORGANISM: Archaeoglobus fulgidus

<400> SEQUENCE: 15

Met Arg Leu Val Val Asp Gly Phe Gly Lys Tyr Leu Gly Ile Glu Asn
1               5                   10                  15

Gly Leu Ile Val Val Lys Glu Lys Gly Lys Ala Leu Arg Lys Val Arg
            20                  25                  30

Pro Glu Asp Leu Lys Gln Val Leu Ile Ile Gly Lys Ala Ala Ile Ser
        35                  40                  45

Ser Asp Ala Ile Lys Leu Leu Lys Asn Arg Val Asp Val Val Phe
50                  55                  60

Leu Asp Phe Asn Gly Glu Ile Leu Gly Arg Leu Ser His Pro Leu Ile
65                  70                  75                  80

Gly Thr Ala Lys Thr Arg Arg Glu Gln Tyr Leu Ala Tyr Gly Asp Lys
                85                  90                  95

Arg Gly Val His Leu Ala Lys Glu Phe Ile Lys Ala Lys Met Ala Asn
            100                 105                 110

Gln Met Ala Ile Leu Thr Asn Leu Ala Lys Ala Arg Lys Asp Ser Asn
        115                 120                 125

Pro Glu Val Ala Glu Ser Leu Leu Lys Ala Lys Lys Glu Ile Asp Ala
    130                 135                 140

Cys Leu Asn Glu Leu Asp Gly Val Glu Ala Glu Met Ile Asp Lys Val
145                 150                 155                 160

Arg Glu Arg Leu Leu Gly Ile Glu Gly Lys Ala Ser Lys His Tyr Trp
                165                 170                 175

Asp Ala Ile Ser Leu Val Ile Pro Glu Glu Tyr Arg Phe Asn Gly Arg
            180                 185                 190

Arg Gly Ile Glu Ile Gly Ser Pro Arg Tyr Ala Lys Asp Ile Val Asn
        195                 200                 205

Ala Met Leu Asn Tyr Gly Tyr Ser Ile Leu Leu Ala Glu Cys Val Lys
    210                 215                 220

Ala Val Glu Leu Ala Gly Leu Asp Pro Tyr Ala Gly Phe Leu His Val
225                 230                 235                 240

Asp Val Ser Gly Arg Ser Ser Leu Ala Ile Asp Leu Met Glu Asn Phe
                245                 250                 255

Arg Gln Gln Val Val Asp Arg Val Val Leu Arg Leu Ile Ser Tyr Arg
            260                 265                 270

Gln Ile Lys Pro Glu Asp Cys Glu Lys Arg Asn Met Val Cys Gln Leu
        275                 280                 285

Ser Asp Asn Ala Arg Arg Leu Leu Ala Ser Leu Leu Glu Arg Leu
    290                 295                 300

Asp Ser Lys Thr Gln Tyr Arg Gly Arg Asn Leu Ala Tyr Ser Ser Ile
305                 310                 315                 320

Ile Leu Leu His Ala Arg Asp Val Val Ala Phe Leu Arg Gly Glu Arg
                325                 330                 335

Arg Tyr Glu Gly Phe Val Gln Lys Trp
            340                 345

<210> SEQ ID NO 16
<211> LENGTH: 328
<212> TYPE: PRT
<213> ORGANISM: Nitrosomonas eutropha

<400> SEQUENCE: 16

Met Thr Ser Leu Phe Val Asp Arg Arg Gly Val Val Leu Glu Leu Glu

```
            1               5                  10                 15
        Ser Gly Ala Ile Val Phe Arg Glu Asn Gly Glu Arg Ile Gly Thr Val
                       20                 25                 30

Pro Ile Ala Pro Leu Thr Arg Val Phe Leu Arg Gly Asp Val Lys Leu
                       35                 40                 45

Pro Ala Ala Leu Leu Gly Lys Leu Gly Glu Gln Gly Val Gly Val Val
                       50                 55                 60

Ile Leu Ser Gly Arg Ile Gly Arg Pro Ser Leu Leu Ala Arg Pro
         65                 70                 75                 80

His Asn Asp Ala Ala Arg Arg Val Val Gln Ile Arg Leu Ser Phe Asp
                       85                 90                 95

Lys Pro Phe Cys Leu Gln Ile Ala Lys Ala Leu Ile Glu Arg Lys Leu
                       100                105                110

Thr Arg Gln Ile Glu Trp Phe Ala Glu Leu Arg Glu Asn Asp Met Gln
                       115                120                125

Val Arg Tyr Glu Leu Ser His Ala Leu Arg Ala Leu Glu Glu His Arg
                       130                135                140

Ser Arg Ile Gly His Val Ser Ser Ala Ala Ser Leu Arg Gly Val Glu
        145                150                155                160

Gly Ser Ala Ala Ala Arg Tyr Phe Ser Gly Leu Gln Ala Val Val Pro
                       165                170                175

Asp Ser Leu His Phe Ser Gly Arg Asn Arg Arg Pro Pro Arg Asp Pro
                       180                185                190

Phe Asn Ala Leu Leu Ser Leu Thr Tyr Thr Leu Leu His Ser Glu Ile
                       195                200                205

Ala Ile Ala Leu Tyr Gly Thr Gly Phe Asp Pro Tyr Val Gly Phe Tyr
                       210                215                220

His Arg Leu Ala Phe Gly Arg Glu Ser Leu Ala Ser Asp Leu Leu Glu
        225                230                235                240

Pro Leu Arg Pro Leu Ala Asp Gln Phe Ala Leu Ala Leu Ile Arg Lys
                       245                250                255

Lys Val Leu Glu Lys Asp His Phe Ser Thr Thr Glu Ala Gly Cys Leu
                       260                265                270

Leu Gly Lys Ala Gly Arg Thr Arg Tyr Tyr Ala Ala Tyr Gly Glu His
                       275                280                285

Ser Glu Thr Leu Arg Lys Gly Ile Asn Gln Glu Ile Glu Trp Leu Thr
                       290                295                300

Ala Gln Val Asn Glu Ile Leu Ala Thr Ala Glu Asp Val Gln Pro
        305                310                315                320

Asp Asp Ser Phe Glu Asp Phe Gly
                       325

<210> SEQ ID NO 17
<211> LENGTH: 338
<212> TYPE: PRT
<213> ORGANISM: Mycobacterium tuberculosis

<400> SEQUENCE: 17

Met Val Gln Leu Tyr Val Ser Asp Ser Val Ser Arg Ile Ser Phe Ala
 1               5                  10                 15

Asp Gly Arg Val Ile Val Trp Ser Glu Glu Leu Gly Glu Ser Gln Tyr
                20                 25                 30

Pro Ile Glu Thr Leu Asp Gly Ile Thr Leu Phe Gly Arg Pro Thr Met
                35                 40                 45
```

```
Thr Thr Pro Phe Ile Val Glu Met Leu Lys Arg Glu Arg Asp Ile Gln
     50                  55                  60

Leu Phe Thr Thr Asp Gly His Tyr Gln Gly Arg Ile Ser Thr Pro Asp
 65                  70                  75                  80

Val Ser Tyr Ala Pro Arg Leu Arg Gln Gln Val His Arg Thr Asp Asp
                 85                  90                  95

Pro Ala Phe Cys Leu Ser Leu Ser Lys Arg Ile Val Ser Arg Lys Ile
                100                 105                 110

Leu Asn Gln Gln Ala Leu Ile Arg Ala His Thr Ser Gly Gln Asp Val
            115                 120                 125

Ala Glu Ser Ile Arg Thr Met Lys His Ser Leu Ala Trp Val Asp Arg
130                 135                 140

Ser Gly Ser Leu Ala Glu Leu Asn Gly Phe Glu Gly Asn Ala Ala Lys
145                 150                 155                 160

Ala Tyr Phe Thr Ala Leu Gly His Leu Val Pro Gln Glu Phe Ala Phe
                165                 170                 175

Gln Gly Arg Ser Thr Arg Pro Pro Leu Asp Ala Phe Asn Ser Met Val
            180                 185                 190

Ser Leu Gly Tyr Ser Leu Leu Tyr Lys Asn Ile Ile Gly Ala Ile Glu
195                 200                 205

Arg His Ser Leu Asn Ala Tyr Ile Gly Phe Leu His Gln Asp Ser Arg
210                 215                 220

Gly His Ala Thr Leu Ala Ser Asp Leu Met Glu Val Trp Arg Ala Pro
225                 230                 235                 240

Ile Ile Asp Asp Thr Val Leu Arg Leu Ile Ala Asp Gly Val Val Asp
                245                 250                 255

Thr Arg Ala Phe Ser Lys Asn Ser Asp Thr Gly Ala Val Phe Ala Thr
            260                 265                 270

Arg Glu Ala Thr Arg Ser Ile Ala Arg Ala Phe Gly Asn Arg Ile Ala
275                 280                 285

Arg Thr Ala Thr Tyr Ile Lys Gly Asp Pro His Arg Tyr Thr Phe Gln
290                 295                 300

Tyr Ala Leu Asp Leu Gln Leu Gln Ser Leu Val Arg Val Ile Glu Ala
305                 310                 315                 320

Gly His Pro Ser Arg Leu Val Asp Ile Asp Ile Thr Ser Glu Pro Ser
                325                 330                 335

Gly Ala

<210> SEQ ID NO 18
<211> LENGTH: 315
<212> TYPE: PRT
<213> ORGANISM: Thermus thermophilus

<400> SEQUENCE: 18

Met Thr Leu His Leu Thr Arg Gln Gly Ala Thr Leu Arg Leu Arg Gln
 1               5                  10                  15

Gly Arg Leu Leu Leu Glu Glu Gly Arg Glu Val Ala Gly Phe Pro
                20                  25                  30

Ala Arg Gln Val Arg Ser Val Ala Leu Trp Gly Asn Val Arg Leu Ser
             35                  40                  45

Thr Pro Ala Leu Val Phe Leu Leu Arg Gln Gly Val Pro Val Phe Phe
     50                  55                  60

Tyr Ser Leu Glu Gly Phe Leu His Gly Val Ala Gly Ala Tyr Pro Asp
 65                  70                  75                  80
```

```
Pro His Pro Ala His Leu Arg Ala Gln Phe Ala Ala Glu Gly Leu Pro
                 85                  90                  95

Leu Ala Arg Ala Phe Val Val Gly Lys Leu Arg Ser Ala Leu Ala Leu
            100                 105                 110

Leu Glu Arg His Arg Leu Pro Glu Ala Gly Val Val Glu Ala Leu
            115                 120                 125

Ala Arg Ala Glu Gly Ala Ser Glu Leu Glu Arg Leu Arg Gly Ala Glu
        130                 135                 140

Gly Glu Gly Ser Arg Val Tyr Phe Gln Gly Leu Ala Arg Leu Leu Gly
145                 150                 155                 160

Pro Tyr Gly Phe Gly Gly Arg Thr Arg Arg Pro Pro Arg Asp Pro Val
                165                 170                 175

Asn Ala Ala Leu Ser Tyr Gly Tyr Ala Leu Leu Leu Gly Arg Val Leu
            180                 185                 190

Val Ala Val Arg Leu Ala Gly Leu His Pro Glu Val Gly Phe Leu His
            195                 200                 205

Ala Glu Gly Arg Arg Ser Pro Ala Leu Ala Leu Asp Leu Met Glu Glu
        210                 215                 220

Phe Arg Val Pro Val Val Asp Gln Val Val Leu Ser Ala Phe Arg Arg
225                 230                 235                 240

Gly Leu Leu Thr Pro Ser His Ala Glu Val Arg Glu Gly Gly Val Tyr
                245                 250                 255

Leu Asn Glu Glu Gly Arg Arg Leu Ile Gln Leu Phe Glu Arg
            260                 265                 270

Leu Leu Glu Gly Val Ser His Pro Leu Gly Phe Arg Lys Pro Leu Gly
            275                 280                 285

Glu Thr Ile Glu Val Gln Ala Gln Arg Leu Lys Ala Ala Leu Leu Gly
        290                 295                 300

Arg Gly Arg Tyr Thr Pro Phe Tyr Leu Trp Arg
305                 310                 315

<210> SEQ ID NO 19
<211> LENGTH: 330
<212> TYPE: PRT
<213> ORGANISM: Thermoanaerobacter tengcongensis

<400> SEQUENCE: 19

Met Gln Lys Thr Leu Tyr Leu Phe Ala Asn Gly Lys Leu Tyr Arg Lys
1               5                   10                  15

Asp Asn Thr Ile Cys Val Glu Gly Glu Lys Glu Lys Tyr Phe Pro
            20                  25                  30

Val Glu Ser Val Arg Asp Ile Tyr Val Phe Gly Glu Val Asp Leu Asn
        35                  40                  45

Lys Lys Phe Ile Glu Phe Ala Glu Glu Lys Glu Ile Ile Leu His Phe
    50                  55                  60

Phe Gly Tyr Tyr Gly Asn Tyr Val Gly Ser Phe Tyr Pro Arg Glu His
65                  70                  75                  80

Tyr Asn Ser Gly Tyr Ile Ile Leu Lys Gln Ala Glu His Tyr Leu Asp
                85                  90                  95

Ser Ala Arg Arg Leu Asp Leu Ala Arg Arg Phe Val Gln Gly Ala Val
            100                 105                 110

Ala Asn Met Thr Gln Val Leu Lys Tyr Tyr Gln Asn Arg Gly Arg Asp
        115                 120                 125

Leu Glu Asp Tyr Leu His Ala Ile Ser Ala Leu Glu Ala Ser Leu Leu
    130                 135                 140
```

```
Ser Val Ser Ser Ile Glu Glu Leu Met Ala Leu Gly Asn Ile Arg
145                 150                 155                 160

Arg Tyr Tyr Tyr Glu Ser Phe Asn Thr Ile Leu Asp Asp Thr Pro Phe
            165                 170                 175

Val Leu Lys Asn Arg Asn Lys Arg Pro Pro Thr Asp Pro Leu Asn Ala
            180                 185                 190

Leu Ile Ser Phe Gly Asn Ser Leu Val Tyr Thr Lys Ile Leu Thr Glu
            195                 200                 205

Ile Tyr Lys Thr His Leu Asp Pro Arg Ile Gly Tyr Leu His Thr Thr
210                 215                 220

Asn Phe Arg Arg Phe Thr Leu Asn Leu Asp Val Ala Glu Ile Phe Lys
225                 230                 235                 240

Pro Ile Tyr Ala Asp Arg Val Leu Phe Thr Leu Leu Lys Lys Asn Ile
            245                 250                 255

Ile Lys Glu Asp Asp Phe Glu Thr Gln Gly Glu Ile Ser Leu Leu Lys
            260                 265                 270

Glu Arg Gly Arg Arg Leu Tyr Val Gln Glu Phe Glu Gly Lys Leu Gln
            275                 280                 285

Thr Thr Phe Tyr His Arg Arg Leu Lys Arg Asn Val Ser Tyr Gln Thr
290                 295                 300

Leu Met Arg Leu Glu Leu Tyr Lys Leu Glu Lys His Leu Ile Gly Glu
305                 310                 315                 320

Glu Leu Tyr Glu Pro Phe Val Ser Arg Trp
            325                 330

<210> SEQ ID NO 20
<211> LENGTH: 319
<212> TYPE: PRT
<213> ORGANISM: Thermotoga maritima

<400> SEQUENCE: 20

Met Glu Ser Val Tyr Leu Phe Ser Ser Gly Thr Leu Lys Arg Lys Ala
 1               5                  10                  15

Asn Thr Ile Cys Leu Glu Thr Glu Ser Gly Arg Lys Tyr Ile Pro Val
            20                  25                  30

Glu Asn Val Met Asp Ile Lys Val Phe Gly Glu Val Asp Leu Asn Lys
            35                  40                  45

Arg Phe Leu Glu Phe Leu Ser Gln Lys Arg Ile Pro Ile His Phe Phe
 50                  55                  60

Asn Arg Glu Gly Tyr Tyr Val Gly Thr Phe Tyr Pro Arg Glu Tyr Leu
 65                  70                  75                  80

Asn Ser Gly Phe Leu Ile Leu Lys Gln Ala Glu His Tyr Ile Asn Gln
            85                  90                  95

Glu Lys Arg Met Leu Ile Ala Arg Glu Ile Val Ser Arg Ser Phe Gln
            100                 105                 110

Asn Met Val Asp Phe Leu Lys Lys Arg Lys Val Arg Ala Asp Ser Leu
            115                 120                 125

Thr Arg Tyr Lys Lys Lys Ala Glu Glu Ala Ser Asn Val Ser Glu Leu
            130                 135                 140

Met Gly Ile Glu Gly Asn Ala Arg Glu Glu Tyr Tyr Ser Met Ile Asp
145                 150                 155                 160

Ser Leu Val Ser Asp Glu Arg Phe Arg Ile Glu Lys Arg Thr Arg Arg
            165                 170                 175

Pro Pro Lys Asn Phe Ala Asn Thr Leu Ile Ser Phe Gly Asn Ser Leu
```

```
                 180               185               190
Leu Tyr Thr Thr Val Leu Ser Leu Ile Tyr Gln Thr His Leu Asp Pro
             195               200               205
Arg Ile Gly Tyr Leu His Glu Thr Asn Phe Arg Arg Phe Ser Leu Asn
         210               215               220
Leu Asp Ile Ala Glu Leu Phe Lys Pro Ala Val Val Asp Arg Leu Phe
225               230               235                       240
Leu Asn Leu Val Asn Thr Arg Gln Ile Asn Glu Lys His Phe Asp Glu
                 245               250               255
Ile Ser Glu Gly Leu Met Leu Asn Asp Glu Gly Lys Ser Leu Phe Val
             260               265               270
Lys Asn Tyr Glu Gln Ala Leu Arg Glu Thr Val Phe His Lys Lys Leu
         275               280               285
Asn Arg Tyr Val Ser Met Arg Ser Leu Ile Lys Met Glu Leu His Lys
     290               295               300
Leu Glu Lys His Leu Ile Gly Glu Gln Val Phe Gly Ser Glu Glu
305               310               315

<210> SEQ ID NO 21
<211> LENGTH: 316
<212> TYPE: PRT
<213> ORGANISM: Aquifex aeolicus

<400> SEQUENCE: 21

Met Gly Arg Val Tyr Tyr Ile Asn Ser His Gly Thr Leu Ser Arg His
1               5                   10                  15
Glu Asn Thr Leu Arg Phe Glu Asn Ala Glu Val Lys Lys Asp Ile Pro
             20                  25                  30
Val Glu Asp Val Glu Glu Ile Phe Val Phe Ala Glu Leu Ser Leu Asn
         35                  40                  45
Thr Lys Leu Leu Asn Phe Leu Ala Ser Lys Gly Ile Pro Leu His Phe
     50                  55                  60
Phe Asn Tyr Tyr Gly Tyr Tyr Thr Gly Thr Phe Tyr Pro Arg Glu Ser
65                  70                  75                  80
Ser Val Ser Gly His Leu Leu Ile Lys Gln Val Glu His Tyr Leu Asp
                 85                  90                  95
Ala Gln Lys Arg Leu Tyr Leu Ala Lys Ser Phe Val Ile Gly Ser Ile
             100                 105                 110
Leu Asn Leu Glu Tyr Val Tyr Lys Ile Ser Ala Asp Thr Tyr Leu Asn
         115                 120                 125
Lys Val Lys Glu Thr Asn Ser Ile Pro Glu Leu Met Ser Val Glu Ala
     130                 135                 140
Glu Phe Arg Lys Leu Cys Tyr Lys Leu Glu Glu Val Thr Gly Trp
145                 150                 155                 160
Glu Leu Glu Lys Arg Thr Lys Arg Pro Gln Asn Pro Leu Asn Ala
                 165                 170                 175
Leu Ile Ser Phe Gly Asn Ser Leu Thr Tyr Ala Lys Val Leu Gly Glu
             180                 185                 190
Ile Tyr Lys Thr Gln Leu Asn Pro Thr Val Ser Tyr Leu His Glu Pro
         195                 200                 205
Ser Thr Lys Arg Phe Ser Leu Ser Leu Asp Val Ala Glu Val Phe Lys
     210                 215                 220
Pro Ile Phe Val Asp Asn Leu Ile Ile Arg Leu Ile Gln Glu Asn Lys
225                 230                 235                 240
```

```
Ile Asp Lys Thr His Phe Ser Thr Glu Leu Asn Met Thr Phe Leu Asn
                245                 250                 255

Glu Ile Gly Arg Lys Val Phe Leu Lys Ala Phe Asn Glu Leu Leu Glu
        260                 265                 270

Thr Thr Ile Phe Tyr Pro Lys Leu Asn Arg Lys Val Ser His Arg Thr
275                 280                 285

Leu Ile Lys Leu Glu Leu Tyr Lys Leu Ile Lys His Leu Leu Glu Glu
        290                 295                 300

Glu Val Tyr Leu Pro Leu Asn Tyr Gly Gly Leu Lys
305                 310                 315
```

<210> SEQ ID NO 22
<211> LENGTH: 324
<212> TYPE: PRT
<213> ORGANISM: Pseudomonas aeruginosa

<400> SEQUENCE: 22

```
Met Asp Asp Ile Ser Pro Ser Glu Leu Lys Thr Ile Leu His Ser Lys
1               5                   10                  15

Arg Ala Asn Leu Tyr Tyr Leu Gln His Cys Arg Val Leu Val Asn Gly
            20                  25                  30

Gly Arg Val Glu Tyr Val Thr Asp Glu Gly Arg His Ser His Tyr Trp
        35                  40                  45

Asn Ile Pro Ile Ala Asn Thr Thr Ser Leu Leu Leu Gly Thr Gly Thr
    50                  55                  60

Ser Ile Thr Gln Ala Ala Met Arg Glu Leu Ala Arg Ala Gly Val Leu
65                  70                  75                  80

Val Gly Phe Cys Gly Gly Gly Gly Thr Pro Leu Phe Ser Ala Asn Glu
                85                  90                  95

Val Asp Val Glu Val Ser Trp Leu Thr Pro Gln Ser Glu Tyr Arg Pro
            100                 105                 110

Thr Glu Tyr Leu Gln Arg Trp Val Gly Phe Trp Phe Asp Glu Glu Lys
        115                 120                 125

Arg Leu Val Ala Ala Arg His Phe Gln Arg Ala Arg Leu Glu Arg Ile
130                 135                 140

Arg His Ser Trp Leu Glu Asp Arg Val Leu Arg Asp Ala Gly Phe Ala
145                 150                 155                 160

Val Asp Ala Thr Ala Leu Ala Val Ala Val Glu Asp Ser Ala Arg Ala
                165                 170                 175

Leu Glu Gln Ala Pro Asn His Glu His Leu Leu Thr Glu Glu Ala Arg
            180                 185                 190

Leu Ser Lys Arg Leu Phe Lys Leu Ala Ala Gln Ala Thr Arg Tyr Gly
        195                 200                 205

Glu Phe Val Arg Ala Lys Arg Gly Ser Gly Gly Asp Pro Ala Asn Arg
    210                 215                 220

Phe Leu Asp His Gly Asn Tyr Leu Ala Tyr Gly Leu Ala Ala Thr Ala
225                 230                 235                 240

Thr Trp Val Leu Gly Ile Pro His Gly Leu Ala Val Leu His Gly Lys
                245                 250                 255

Thr Arg Arg Gly Gly Leu Val Phe Asp Val Ala Asp Leu Ile Lys Asp
            260                 265                 270

Ser Leu Ile Leu Pro Gln Ala Phe Leu Ser Ala Met Arg Gly Asp Glu
        275                 280                 285

Glu Gln Asp Phe Arg Gln Ala Cys Leu Asp Asn Leu Ser Arg Ala Gln
    290                 295                 300
```

```
Ala Leu Asp Phe Met Ile Asp Thr Leu Lys Asp Val Ala Gln Arg Ser
305                 310                 315                 320

Thr Val Ser Ala

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
caccatggac gacatttctc ccag                                          24

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
ttatcatgcg gatactgtgc tc                                            22
```

METHODS OF GENERATING NUCLEIC ACID FRAGMENTS

CROSS-REFERENCE

This application claims the benefit of U.S. Provisional Patent Application No. 61/312,510, filed Mar. 10, 2010, which application is incorporated herein by reference in its entirety.

BACKGROUND

Nucleases are enzymes that degrade nucleic acids (e.g., deoxyribonucleic acids, DNA, and ribonucleic acids, RNA) and exist in various biological materials. These enzymes are involved in DNA and RNA metabolism, including degradation, synthesis and genetic recombination of nucleic acids. Nucleases are generally classified into exonucleases and endonucleases according to their mode of action. The former type acts on the terminus of a nucleic acid molecule and hydrolyzes the chain progressively to liberate nucleotides, while the latter type cleaves a phosphodiester bond in a nucleic acid molecule distributively to produce DNA or RNA fragments or oligonucleotides.

Deoxyribonucleases (DNases) are phosphodiesterases capable of hydrolyzing polydeoxyribonucleic acid. DNases have been purified from various species to various degrees. Among other uses, DNases find use as reagents in a variety of protocols in molecular biology. DNases have also been used for therapeutic purposes, for example, to reduce the viscosity of pulmonary secretions in such diseases as pneumonia and cystic fibrosis, thereby aiding in the clearing of respiratory airways.

Literature

Makarova et al. (2002) *Nucleic Acids Res* 30:482-496; Makarova et al. (2006) *Biology Direct* 1:1-26; Wiedenheft et al. (2009) *Structure* 17:904.

SUMMARY

The present disclosure provides methods of using a Cas1 polypeptide to generate nucleic fragments from a DNA substrate. These methods may be used in vitro or in vivo. Also provided are methods of screening for modulators of Cas1.

BRIEF DESCRIPTION OF THE DRAWINGS

FIGS. 9A to 9F depict Cas1 amino acid sequences (SEQ ID NOs:1-21).

FIG. 10 depicts an amino acid sequence of a *Pseudomonas aeruginosa* Cas1 polypeptide (SEQ ID NO:22).

DEFINITIONS

Figure 1:
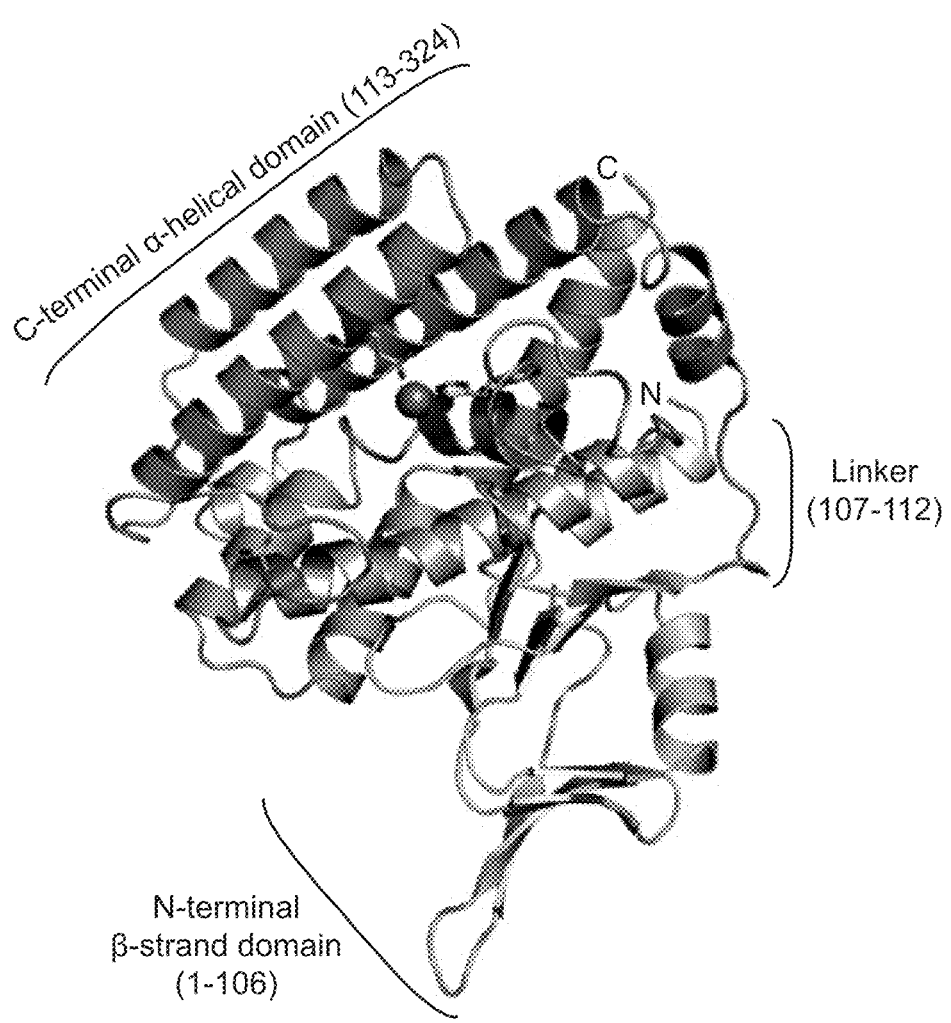
FIG. 1 depicts crystal structure of the Cas1 protein from *Pseudomonas aeruginosa*.

The term "biofilm" as used herein refers to an aggregate of microorganisms in which the microorganisms adhere to one another and/or to a surface. Such microorganisms can be embedded within a self-produced matrix of extracellular polymeric substance (EPS). Biofilm EPS, which is also referred to as "slime", is a mixture of extracellular DNA, proteins, and polysaccharides. Biofilms may form on living or non-living surfaces, and represent a prevalent mode of microbial life in natural, industrial and hospital settings.

"Reducing or inhibiting" in reference to a biofilm refers to the prevention of biofilm formation or growth, reduction in the rate of biofilm formation or growth, partial or complete inhibition of biofilm formation or growth.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that and in the appended claims, the singular forms "a," "an," and "the" include plural referents unless the context clearly dictates otherwise. Thus, for example, reference to "a method" includes a plurality of such methods and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Provided herein are methods of using Cas1 to generate nucleic fragments from a DNA substrate. These methods may be used in vitro or in vivo. Also provided are methods of screening for modulators of Cas1.

Methods of Generating Nucleic Acid Fragments

The present disclosure provides methods for generating nucleic acid fragments of substantially uniform length from a DNA substrate. The methods generally involve contacting a DNA substrate with a Cas1 polypeptide.

"Cas1" polypeptide refers to CRISPR associated (Cas) protein1. CRISPR Clustered, regularly interspaced, short palindromic repeats is an acronym that describes the architecture of these repetitive elements. Cas1 (COG1518 in the Clusters of Orthologous Group of proteins classification system) is the best marker of the CRISPR-associated systems (CASS). Based on phylogenetic comparisons, seven distinct versions of the CRISPR-associated immune system have been identified (CASS1-7).

Cas1 polypeptide used in the methods described herein can be any Cas1 polypeptide present in a prokaryote. In certain embodiments, a Cas1 polypeptide is a Cas1 polypeptide of an archaeal microorganism. In certain embodiments, a Cas1 polypeptide is a Cas1 polypeptide of a Euryarchaeota microorganism. In certain embodiments, a Cas1 polypeptide is a Cas1 polypeptide of a Crenarchaeota microorganism. In certain embodiments, a Cas1 polypeptide is a Cas1 polypeptide of a bacterium. In certain embodiments, a Cas1 polypeptide is a Cas1 polypeptide of a gram negative or gram positive bacteria. In certain embodiments, a Cas1 polypeptide is a Cas1 polypeptide of *Pseudomonas aeruginosa*. In certain embodiments, a Cas1 polypeptide is a Cas1 polypeptide of *Aquifex aeolicus*. In certain embodiments, a Cas1 polypeptide is a Cas1 polypeptide that is a member of one of CASS1-7. In certain embodiments, Cas1 polypeptide is a Cas1 polypeptide that is a member of CASS3. In certain embodiments, a Cas1 polypeptide is a Cas1 polypeptide that is a member of CASS7. In certain embodiments, a Cas1 polypeptide is a Cas1 polypeptide that is a member of CASS3 or CASS7.

In some embodiments, a Cas1 polypeptide is encoded by a nucleotide sequence provided in GenBank at, e.g., GeneID number: 2781520, 1006874, 9001811, 947228, 3169280, 2650014, 1175302, 3993120, 4380485, 906625, 3165126, 905808, 1454460, 1445886, 1485099, 4274010, 888506, 3169526, 997745, 897836, or 1193018.

In certain embodiments, a Cas1 polypeptide comprises an amino acid sequence having at least about 80%, at least about 85%, at least about 90%, at least about 95%, at least about 98%, at least about 99%, or 100%, amino acid identity to a contiguous stretch of from about 100 amino acids (aa) to about 150 aa, from about 150 aa to about 200 aa, from about 200 aa to about 250 aa, from about 250 aa to about 275 aa, from about 275 aa to about 300 aa, from about 300 aa to about 325 aa, up to the full length, of an amino acid sequence provided in FIG. 9. In certain embodiments, Cas1 polypeptide is a Cas1 polypeptide whose amino acid sequence is provided in FIG. 9.

In some embodiments, a Cas1 polypeptide comprises an amino acid sequence having at least about 80%, at least about 85%, at least about 90%, at least about 95%, at least about 98%, at least about 99%, or 100%, amino acid identity to a contiguous stretch of from about 100 amino acids (aa) to about 150 aa, from about 150 aa to about 200 aa, from about 200 aa to about 250 aa, from about 250 aa to about 275 aa, from about 275 aa to about 300 aa, from about 300 aa to about 324 aa, of the amino acid sequence depicted in FIG. 10.

In certain embodiments, Cas1 protein may be a "functional derivative" of a naturally occurring Cas1 protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. A "fusion" polypeptide is a polypeptide comprising a polypeptide or portion (e.g., one or more domains) thereof fused or bonded to heterologous polypeptide. Examples of fusion polypeptides include immunoadhesins which combine a portion of the Cas1 protein with an immunoglobulin sequence, and epitope tagged polypeptides, which may comprise a Cas1 protein, for example, or portion thereof fused to a "tag polypeptide". The tag polypeptide has enough residues to provide an epitope against which an antibody can be made, yet is short enough such that it does not interfere with nuclease activity of Cas1. Suitable tag polypeptides generally have at least six amino acid residues and usually between about 6-60 amino acid residues.

"Cas1 polypeptide" encompasses a full-length Cas1 polypeptide, an enzymatically active fragment of a Cas1 polypeptide, and enzymatically active derivatives of a Cas1 polypeptide or fragment thereof. Suitable derivatives of a Cas1 polypeptide or a fragment thereof include but are not limited to mutants, fusions, covalent modifications of Cas1 protein or a fragment thereof. Cas1 protein which includes Cas1 protein or a fragment thereof, as well as derivatives of Cas1 protein or a fragment thereof, may be obtainable from a cell or synthesized chemically or by a combination of these two procedures. The cell may be a cell that naturally produces Cas1 protein, or a cell that naturally produces Cas1 protein and is genetically engineered to produce the endogenous Cas1 protein at a higher expression level or to produce a Cas1 protein from an exogenously introduced nucleic acid, which nucleic acid encodes a Cas1 that is same or different from the endogenous Cas1. In some case, the cell does not naturally produce Cas1 protein and is genetically engineered to produce a Cas1 protein.

Mutants of Cas1 protein may be generated by performing conservative substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids. In certain cases, the conserved residues may not be substituted and the substitutions limited to the non-conserved residues.

In certain embodiments, the Cas1 protein may be purified from an organism. The organism may be producing the Cas1 protein from an endogenous gene or from an exogenous gene. The exogenous gene may be present in the organism transiently or stably. For example, a polynucleotide encoding a Cas1 protein can be introduced into a suitable expression vector. The expression vector is introduced into a suitable cell. Expression vectors generally have convenient restriction sites located near the promoter sequence to provide for the insertion of polynucleotide sequences. Transcription cassettes may be prepared comprising a transcription initiation region, cas1 gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

Cas1 protein may be recovered and purified from recombinant cell cultures by well-known methods including ammonium sulfate or ethanol precipitation, acid extraction, anion or cation exchange chromatography, phosphocellulose chromatography, hydrophobic interaction chromatography, high performance liquid chromatography, affinity chromatography, protein G affinity chromatography, for example, hydroxyapatite chromatography and lectin chromatography, etc.

Cas1 protein may also be recovered from: products of purified cells, whether directly isolated or cultured; products of chemical synthetic procedures; and products produced by recombinant techniques from a prokaryotic or eukaryotic host, including, for example, bacterial, yeast higher plant, insect, and mammalian cells.

As mentioned above, methods for generating nucleic acid fragments of substantially uniform length from a DNA substrate are provided. The methods include contacting the DNA substrate with a Cas1 polypeptide.

The duration of the contacting step may be about 0.1 hour-48 hours, for example, from about 0.1 hour to about 0.2 hour, from about 0.2 hour to about 0.3 hour, from about 0.3 hour to about 0.5 hour, from about 0.5 hour to about 1 hour, from about 0.3 hour to about 46 hours, about 0.5 hour-45 hours, about 1 hour-40 hours, about 2 hours-35 hours, about 4 hours-30 hours, about 6 hours-24 hours, about 8 hours-20 hours, about 10 hours-18 hours, or about 12 hours-16 hours, such as, 0.3 hour, 0.5 hour, 1 hour, 3 hours, 10 hours, 13 hours, 16 hours, or 18 hours.

The amount of Cas1 that is employed is one that is from about 10 units/ml-50,000 units/ml, for example, from about 20 units/ml-30,000 units/ml, about 30 units/ml-10,000 units/ml, about 50 units/ml-5000 units/ml, about 100 units/ml-3000 units/ml, about 200 units/ml-2000 units/ml, about 300 units/ml-1000 units/ml, such as, about 100 units/ml, 300 units/ml, 1000 units/ml, 2000 units/ml, 5000 units/ml, 10,000 units/ml, 20,000 units/ml, or 50,000 units/ml.

The temperature at which the enzymatic reaction is carried out is can be from 4° C.-50° C., for example, about 10° C.-45° C., about 16° C.-40° C., about 20° C.-37° C., about 25° C.-35° C., about 30° C.-33° C., e.g., 10° C., 18° C., 25° C., 30° C., 37° C., or 45° C.

The contacting step may be carried out in conditions suitable for Cas1 endonuclease activity. In certain embodiments, the conditions suitable for Cas1 endonuclease activity are conditions in which a divalent metal ion such as magnesium ($Mg^{2+}$) is present. In these embodiments, $Mg^{2+}$ concentration may range from about 1 mM-25 mM, for example, about 1.5 mM-20 mM, about 2 mM-15 mM, about 2 mM-10 mM, about 3 mM-8 mM, or about 5 mM-6 mM, such as, 2 mM, 2.5 mM, 3 mM, or 5 mM.

In certain embodiments, the conditions suitable for Cas1 endonuclease activity are conditions in which a divalent metal ion such as Manganese ($Mn^{2+}$) is present. In these embodiments, the $Mn^{2+}$ concentration may range from about 1 mM-25 mM, for example, about 1.5 mM-20 mM, about 2 mM-15 mM, about 2 mM-10 mM, about 3 mM-8 mM, or about 5 mM-6 mM, such as, 2 mM, 2.5 mM, 3 mM, or 5 mM.

Under the conditions suitable for Cas1 endonuclease activity, the pH typically ranges from about pH 4.5-pH 10, for example, pH 5-pH 8.5, pH 7-pH 8.5, or pH 7-pH 8, such as, pH 7, pH 7.5, pH 8, or pH 8.5.

The DNA substrate may be in the form of genomic DNA, linear DNA, circular DNA, double or single stranded DNA, or a mixture of two or more of these forms of DNA. The DNA substrate may be from any organism, for example, viruses, prokaryotes, e.g. bacteria, archaea and cyanobacteria; and eukaryotes, e.g., members of the kingdom protista, such as flagellates, amoebas and the like, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, combjellies, worms, rotifers, roundworms, annelids, molluscs, arthropods, echinoderms, acorn worms, and vertebrates, including reptiles, fishes, birds, snakes, and mammals, e.g. rodents, primates, including humans, and the like. DNA substrates may be obtained from biological fluids, e.g., blood; tissue samples; or cells (including cell lines, cell cultures, etc.), for example. The DNA substrate may be used directly from its naturally occurring source and/or preprocessed in a number of different ways, as is known in the art.

The DNA substrate can be present in a living cell, or can be isolated from a living cell. For example, the DNA substrate can be present in a cell lysate. In some embodiments, the DNA substrate is isolated, and can be purified, e.g., the DNA substrate can be at least about 50% pure, at least about 60% pure, at least about 70% pure, at least about 80% pure, at least about 85% pure, at least about 90% pure, at least about 95% pure, at least about 98% pure, at least about 99%, or greater than 99% pure, e.g., free of macromolecules other than the DNA substrate, and free of other contaminants.

The term "substantially uniform length" when used in reference to nucleic acid fragments, is used to refer to a population of nucleic acid fragments wherein a majority of the fragments have the same length within an acceptable variation. For example, the acceptable variation in the length of a given fragment in the population can be at most 0.1%, 1%, 2%, 5%, 8%, 10%, or 20% of the average length of fragments in the population. This can be a variation in length of at most about 1 nucleotide, 2 nucleotides, 3 nucleotides, 4 nucleotides, 5 nucleotides, 8 nucleotides, 10 nucleotides, 13 nucleotides, 16 nucleotides, 18 nucleotides, 20 nucleotides, 25 nucleotides, 30 nucleotides, 35 nucleotides, 40 nucleotides, 45 nucleotides, 50 nucleotides, 55 nucleotides, or 60 nucleotides. The population can be composed of at least 50%, 60%, 70%, 80%, 90%, 95%, 99% or 99.9% fragments having a particular length.

The substantially uniform length of the nucleic acid fragments generated by contacting a DNA substrate with Cas1 polypeptide may be about 20 base pairs (bp)-1000 bp long, or about 30 bp-750 bp long, or about 40 bp-500 bp long, or about 45 bp-250 bp long, or about 50 bp-200 bp long, or about 60 bp-150 bp long, or about 70 bp-100 bp long, for example, about 30 bp, or about 50 bp, or about 80 bp, or about 100 bp, or about 150 bp, or about 200 bp. About as used herein refers to the value or range indicated ±1 bp, or 2 bp, or 3 bp, or 4 bp, or 5 bp.

In practicing the subject methods, the order in which the various reagents are contacted with the DNA substrate may vary. As such, in certain embodiments, the Cas1 endonuclease may be introduced into a reaction mix after the introduction of any other reagents, e.g., $Mn^{2+}$. In some embodiments, the Cas1 endonuclease may be introduced into the reaction mix before the introduction of some other reagents, e.g., adapter oligonucleotides. The manner in which contacting is achieved may vary, e.g., by introducing Cas1 endonuclease into the reaction mix, by introducing an amount of DNA substrate in a Cas1 endonuclease containing reaction mix, etc.

Screening Methods

Methods for identifying modulators of Cas1 endonuclease activity are provided. The methods may comprise assaying the nuclease activity of Cas1 in the presence of a candidate agent wherein an increase or decrease in Cas1 endonuclease activity identifies the candidate agent as a modulator of Cas1 endonuclease activity.

Candidate agents of interest for screening include biologically active agents of numerous chemical classes, primarily organic molecules, although including in some instances, inorganic molecules, organometallic molecules, immunoglobulins, genetic sequences, etc. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in nuclease activity.

The assaying may comprise contacting the candidate agent to a reaction mix that includes Cas1, a source of divalent metal ion, and a DNA substrate; measuring the activity of Cas1 in the reaction mix, comparing the measured activity to the activity of a control reaction mix that includes Cas1, a source of divalent metal ion, and a DNA substrate but not the candidate agent being tested; and identifying a candidate agent that increases or decreases the Cas 1 endonuclease activity.

Any type of nuclease assay may be used. In certain examples, the assay may be plasmid DNA digestion assays, such as, supercoiled DNA digestion assay or linear DNA digestion assay, or a hyperchromicity assay.

Plasmid DNA Digestion Assays

A supercoiled plasmid DNA digestion assay measures the conversion of supercoiled double-stranded plasmid, e.g., pBR322 DNA to relaxed (nicked), linear, and fragmented forms. The linear DNA digestion assay measures the conversion of linear double-stranded DNA to degraded forms.

Cas1 protein with or without a candidate agent may be added to a solution containing supercoiled double-stranded plasmid or linear double-stranded DNA in an appropriate reaction mix including a buffer, bovine serum albumin (BSA), salt, divalent metal ion, etc. and incubated at around 25° C. At various times, aliquots of the reaction mixtures may be removed and quenched by the addition of a metal chelator, such as, 25 mM EDTA (ethylene-diamine-tetraacetic acid), together with reagents for electrophoretic analysis of DNA, such as, xylene cyanol, bromphenol blue, and glycerol. The integrity of the supercoiled or linear DNA in the quenched samples may be analyzed by electrophoresis of the samples on agarose gels (for example, 0.8% weight/vol.). After electrophoresis, the gels may be stained with a solution of ethidium bromide and the DNA in the gels visualized by ultraviolet light. The relative amounts of supercoiled, relaxed, and linear forms of plasmid DNA may be determined by scanning of the gels with a FluorImager and quantitating the amount of DNA in the bands of the gel that corresponded to those different forms.

In the supercoiled DNA digestion assay, the overall activity of the Cas1 may be measured as the initial rate of disappearance of supercoiled DNA (as a result of it being converted to relaxed (nicked), linear, or degraded DNA), normalized relative to the rate observed with Cas1 without candidate agent. The ratio of linearized to relaxed forms of DNA may also be determined relative to that observed with Cas1 without candidate agent. In the linear DNA digestion assay, the activity of Cas1 with candidate agent may be measured as the initial rate of disappearance of linear DNA (as a result of it being converted to degraded forms), normalized relative to the rate observed with Cas1 without candidate agent.

Modulators of Cas1 endonuclease activity that increase Cas1 activity may be used in vitro or in vivo to enhance Cas1 activity. For instance, such modulators may be added to compositions of Cas1 or used in cell cultures in a laboratory setting. For example, such modulators may serve to enhance the activity of an endogenous Cas1 expressed by a cell in a cell culture and provide an enhanced protection to infection by phages and other pathogens.

Modulators of Cas1 endonuclease activity that decrease Cas1 activity may be used in vitro or in vivo to decrease Cas1 activity. For instance, such modulators may be used to increase the susceptibility of an organism that utilizes Cas1 to defend against viral or other pathogens to such pathogens. Therefore, Cas1 modulators that decrease Cas1 activity may be used to weaken an organism, for example.

Utility

Nucleic Acid Analysis

Cas1 may be used to generate DNA fragments for use in a variety of research and diagnostic methods. For example, the nucleic acid fragments of substantially uniform length generated by using Cas1 may be used for sequencing, genotyping, copy number variation analysis, DNA methylation analysis, and the like.

In some embodiments, the nucleic acid fragments of substantially uniform size generated by using Cas1 do not usually require size selection by a size separation method such as gel purification and as such almost all of the nucleic acid fragments are available for subsequent use. This is especially advantageous in analysis of nucleic acid from samples where the amount of material is limited, such as biopsies, laser captured cells, limited archival tissues, embryoid bodies, small model systems, and difficult to cultivate organisms such as *Microsporidia*.

Nucleic Acid Fragment Libraries

The nucleic acid fragments of substantially uniform size range generated by using Cas1 may include fragments with blunt ends and/or 3' and 5' overhanging ends. The fragment ends may be repaired using methods or kits known in the art to generate ends that are convenient, for example, for insertion into blunt sites in cloning vectors or for ligation of adapters onto the ends of each fragment.

Nucleic acid fragment libraries may be prepared from the nucleic acid fragments. Following end repair, double stranded adaptor polynucleotide sequences may be ligated to both ends of the nucleic acid fragments to form adaptor-fragment-adaptor polynucleotide sequences.

Ligation methods are known in the art and utilize standard methods (Sambrook and Russell, Molecular Cloning, A Laboratory Manual, third edition Cold Spring Harbor Laboratory Press (2001)). Such methods utilize ligase enzymes such as DNA ligase to effect or catalyze joining of the ends of the two polynucleotide strands of, in this case, the adaptor duplex construct and the nucleic acid fragment, such that covalent linkages are formed.

The adaptor constructs may also contain a region on one, or both, of the strands that does not hybridize with a sequence on the other strand of the adaptor. Such "mismatched" adaptors can serve as priming sites for amplification reactions. Optionally, the adaptor-fragment-adaptor molecules may be purified from any components of the ligation reaction, such as enzymes, buffers, salts and the like. Suitable purification methods are known in the art and utilize standard methods (Sambrook and Russell, Supra).

In further embodiments, the adaptor-fragment-adaptor molecules may be amplified. The contents of an amplification reaction are known by one skilled in the art and include appropriate reagents (such as, deoxyribonucleotide triphosphates (dNTPs)), enzymes (e.g. a DNA polymerase) and buffer components required for an amplification reaction. Generally amplification reactions use at least two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical.

The nucleic acid fragment libraries comprising cloned nucleic acid fragments or nucleic acid fragment to which adapters have been ligated may be used in research or diagnostic methods.

Generating Labeled Probes

The nucleic acid fragments generated by using Cas1 may be labeled to generate labeled nucleic acid fragments that can be used a probes, e.g., for use in research and/or diagnostic methods.

Any label detectable by spectroscopic, photochemical, biochemical, immunochemical, electrical, optical or chemical means may be used to label the nucleic acid fragments. Useful labels include biotin for staining with labeled streptavidin conjugate, magnetic beads (e.g., Dynabeads™), fluorescent dyes (e.g., fluorescein, texas red, rhodamine, green fluorescent protein, cyanins and the like), radiolabels (e.g., $^3$H, $^{35}$S, $^{14}$C, or $^{32}$P, enzymes (e.g., horseradish peroxidase, alkaline phosphatase and others commonly used in enzyme-linked immunosorbent assay), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, which are herein incorporated by reference.

The labels may be incorporated into the nucleic acid fragments by any of a number of means well known to those of skill in the art. The label may be simultaneously incorporated during the amplification step. Thus, for example, polymerase chain reaction (PCR) with labeled primers or labeled nucleotides will provide a labeled amplification product. In certain embodiment, a label may be added directly to the nucleic acid fragments or to the amplification product after the amplification is completed. Means of attaching labels to nucleic acids are well known to those of skill in the art and include, for example nick translation or end-labeling, by kinasing of the nucleic acid and subsequent attachment of a nucleic acid linker joining the nucleic acid to a label. Standard methods may be used for labeling a polynucleotide fragment, for example, as set out in Maniatis et al., Molecular Cloning, A Laboratory Manual, Cold Spring Harbor Publication (1982).

Sequencing

Any suitable method of sequencing may be used to determine a sequence read of the nucleic acid fragments prepared using Cas1. Suitable methods of sequencing include the use of sequencing by addition of nucleotide bases, for example sequencing by synthesis (SBS) using nucleoside triphosphates and DNA polymerases (as described in US 2007/0166705 and US 2006/0240439 respectively), or using oligonucleotide cassettes and ligases (as described in U.S. Pat. No. 6,306,597, US 2008/0003571 or Science, 309:5741, 1728-1732 (2005)).

In "sequencing by synthesis" or SBS a new polynucleotide strand base-paired to a template strand is built up in the 5' to 3' direction by successive incorporation of individual nucleotides complementary to the template strand. In one embodiment of SBS the different nucleotide triphosphates used in the sequencing reaction are each labeled with different labels permitting determination of the identity of the incorporated nucleotide as successive nucleotides are added. The labeled nucleotide triphosphates also have a 3' blocking group which prevents further incorporation of complementary bases by the polymerase. The label of the incorporated base can then be determined and the blocking group removed to allow further polymerization to occur. Labeled nucleotides are described in WO07135368.

Sequencing multiple nucleic acid fragments produced by Cas1 may be performed in parallel using arrays, wherein multiple polynucleotide fragments (with or without adapters) are immobilized on an array and are sequenced in parallel. For example, nucleotide(s) is(are) incorporated into a strand of nucleic acid complementary to the template nucleic and each nucleotide is fluorescently labeled. The inclusion of a fluorescent label facilitates detection/identification of the base present in the incorporated nucleotide(s). Appropriate fluorophores are well known in the art. Use of the polynucleotide fragments of substantially uniform size in nucleic acid analysis is described in US Application Publication No. 20090191563, which is herein incorporated by reference.

Treatment Methods

Biofilms

Cas1 polypeptide may be used to reduce or inhibit biofilms.

Biofilms form on living and non-living surfaces and represent a prevalent mode of microbial life in natural, industrial and hospital settings. Biofilms have been found to be involved in a wide variety of microbial infections in the body, by one estimate 80% of all infections. Infectious processes in which biofilms have been implicated include common problems such as urinary tract infections, catheter infections, middle-ear infections, formation of dental plaque, gingivitis, and less common but more lethal processes such as endocarditis, infections in cystic fibrosis, and infections of permanent indwelling devices such as joint prostheses and heart valves. More recently it has been noted that bacterial biofilms may impair cutaneous wound healing and reduce topical antibacterial agents' efficiency in healing or treating infected skin wounds. Biofilms can also form on the inert surfaces of implanted devices such as catheters, prosthetic cardiac valves and intrauterine devices.

Cas1 protein may be employed to prevent microorganisms from adhering to surfaces or growing on surfaces, which surfaces may be porous, soft, hard, semi-soft, semi-hard, regenerating, or non-regenerating. These surfaces include, but are not limited to, polyurethane, metal, alloy, or polymeric surfaces in medical devices, enamel of teeth, and cellular membranes in animals, preferably, mammals, more preferably, humans. The surfaces may be coated or impregnated with the Cas1 protein prior to use. Alternatively, the surfaces may be treated with Cas1 protein to control, reduce, or eradicate the microorganisms adhering to these surfaces.

Cas1 may be used to reduce the viscoelasticity of DNA-containing material, including sputum, mucus, or other pulmonary secretions of patients with pulmonary disease. Abnormal viscous or inspissated secretions (e.g., sputum, mucus, or other pulmonary secretions) are common in pulmonary diseases such as acute or chronic bronchial pneumonia, including infectious pneumonia, bronchitis or tracheobronchitis, bronchiectasis, cystic fibrosis, asthma, tuberculosis, and fungal infections. For such therapies, a solution or finely divided dry preparation of Cas1 may be instilled in conventional fashion into the airways (e.g., bronchi) or lungs of a patient, for example by aerosolization.

Cas1 polypeptide can also useful for treatment of abscesses or severe closed-space infections in conditions such as emphysema, meningitis, abscess, peritonitis, sinusitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. Cas1 may improve the efficacy of antibiotics used in the treatment of such infections (e.g., gentamicin activity is markedly reduced by reversible binding to intact DNA).

Cas1 protein may contribute to the treatment of cystic fibrosis. In cystic fibrosis, *Pseudomonas aeruginosa* reside on the lungs of cystic fibrosis patients. Cas1 protein may prevent, reduce, or eradicate the biofilm of *Pseudomonas aeruginosa*.

Cas1 polypeptide can be used as a preprocedural rinse for surgery, as an antiseptic rinse, a topical antiseptic and a catheter lock solution.

Cas1 polypeptide may also be used for enhancing efficacy of antibiotic therapy against bacterial infections by administration of a pharmaceutical composition of Cas1 polypeptide in combination with or prior to administration of an antibiotic.

Cas1 protein or active fragment or derivative thereof can be incorporated in a liquid disinfecting solution. Such solutions may further comprise antimicrobials or antifungals such as alcohol, providone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws.

Cas1 protein may be formulated into a variety of formulations for therapeutic administration. More particularly, Cas1 protein as disclosed herein can be formulated into pharmaceutical compositions by combination with appropriate pharmaceutically acceptable carriers or diluents, and may be formulated into preparations in solid, semi-solid, liquid forms, such as, powders, granules, solutions, injections, inhalants, gels, hydrogels, microspheres, etc. Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

A pharmaceutical composition comprising Cas1 polypeptide may be an oral preparation, an injection or an aerosol preparation. Preparations suitable for oral administration may be a liquid obtained by dissolving an effective amount of Cas 1 in diluents such as water, physiological saline, a capsule, a sachet or a tablet containing an effective amount of Cas1, suspension containing an effective amount of Cas1suspended in an appropriate dispersion medium, and emulsion prepared by suspending a solution containing an effective amount of Cas1 dissolved in an appropriate dispersion medium and emulsifying the suspension. The aerosol preparation may include Cas1 compressed with dichlorodifluoromethane, propane or nitrogen or a non-compressed preparation such as nebulizer and atomizer, and can be administered by inhalation or spraying into airways and the like.

A Cas1 pharmaceutical composition may be combined with or administered in concert with one or more other pharmacologic agents, such as antibiotics, bronchodilators, anti-inflammatory agents, mucolytics (e.g. n-acetyl-cysteine), actin binding or actin severing proteins (e.g., gelsolin; Matsudaira et al., Cell 54:139-140 (1988); Stossel, et al., PCT Patent Publication No. WO 94/22465 (published Oct. 13, 1994)), protease inhibitors, gene therapy product (e.g., comprising the cystic fibrosis transmembrane conductance regulator (CFTR) gene, Riordan, et al., Science 245:1066-1073 (1989)), glucocorticoids, or cytotoxic agents.

The pharmaceutical composition can also include any of a variety of stabilizing agents, such as an antioxidant for example. The Cas1 polypeptide of a composition can also be complexed with molecules that enhance its in vivo attributes. Such molecules include, for example, carbohydrates, polyamines, amino acids, other peptides, ions (e.g., sodium, potassium, calcium, magnesium, manganese), and lipids. Cas1 may be incorporated into liposomes or microvesicles.

Wound dressings including but not limited to sponges or gauzes can be impregnated with a composition comprising Cas1 polypeptide or active fragment or derivative thereof to prevent or inhibit bacterial or fungal attachment and reduce the risk of wound infections. Similarly, catheter shields as well as other materials used to cover a catheter insertion sites can be coated or impregnated with Cas1 polypeptide or active fragment or derivative thereof to inhibit bacterial or fungal biofilm attachment thereto. Adhesive drapes used to prevent wound infection during high risk surgeries can be impregnated with the isolated protein or active fragment or variant thereof as well. Additional medical devices which can be coated with Cas1 polypeptide or active fragment or derivative thereof include, but are not limited, central venous catheters, intravascular catheters, urinary catheters, Hickman catheters, peritoneal dialysis catheters, endotracheal catheters, mechanical heart valves, cardiac pacemakers, arteriovenous shunts, scleral buckles, prosthetic joints, tympanostomy tubes, tracheostomy tubes, voice prosthetics, penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, PBS (pH approximately 7.5) and bicarbonate buffer (pH approximately 9.0).

The pharmaceutical compositions can be administered for prophylactic and/or therapeutic treatments. Toxicity and therapeutic efficacy of a Cas1 polypeptide can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from cell culture and/or animal studies can be used in formulating a range of dosages for humans. The dosage of an active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile.

The pharmaceutical compositions may be administered using any medically appropriate routes, e.g., an epithelial route such as intranasal, pulmonary, sublingual, oral, buccal, or other routes such as intravascular (intravenous, intraarterial, intracapillary), injection into the cerebrospinal fluid, intracavity or direct injection into a tissue.

The effective amount of a therapeutic composition to be given to a particular patient will depend on a variety of factors, several of which will be different from patient to patient. Utilizing ordinary skill, the competent clinician will be able to optimize the dosage of a particular therapeutic in the course of routine clinical trials.

Kits

Also provided herein are kits that include one or more containers of the components of the compositions described herein.

A subject kit includes at least an isolated Cas1 polypeptide. In some embodiments, the Cas1 polypeptide is lyophilized. In some embodiments, the containers may include a lyophilized Cas1 polypeptide. In some embodiments, the containers may include Cas1 polypeptide suspended in an aqueous medium, where the aqueous medium may be a buffer, for example, PBS, Tris-buffered saline, Tris-Hydrochloride. The medium may include addition components, such as glycerol, or other agents, for example, BSA, dithiothreitol (DTT), that stabilize proteins. The medium may further comprise salt (e.g., sodium chloride, or potassium chloride), additives to prevent microbial growth, such as EDTA, EGTA (ethylene glycol tetra-acetic acid). The kit may further include a container of reaction buffer which may be used in a reaction mixture comprising Cas1 polypeptide. The reaction buffer may include a divalent metal ion, for example, $Mg^{2+}$ or $Mn^{2+}$. In addition the reaction buffer may include one or more of: a buffer, one or more salts, glycerol, DTT, BSA, etc. Other suitable components include, e.g., a nuclease inhibitor, a protease inhibitor, and the like.

In some cases, the kit may include a first container comprising a Cas1 polypeptide; and a second container comprising at least a second component, e.g., a solution comprising a divalent metal ion, for example, $Mg^{2+}$ or $Mn^{2+}$; a protease inhibitor; a nuclease inhibitor; etc. In some case, the kit may include a first container comprising a Cas1 polypeptide and a divalent metal ion, for example, $Mg^{2+}$ or $Mn^{2+}$. In some case, the kit may include a first container comprising a Cas1 polypeptide and a divalent metal ion, for example, $Mg^{2+}$ or $Mn^{2+}$; and a second container comprising a reaction buffer.

The kits may further include a suitable set of instructions, generally written instructions, relating to the use of a Cas1 polypeptide for hydrolyzing a DNA substrate in vitro or in vivo.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); and the like.

Materials and Methods

PA14_Cas1 expression and purification. Genomic DNA isolated from strain 14 of P. aeruginosa (PA14) was used as the template for PCR amplification of the cas1 gene (PA14_33350; GeneID: 4380485) (Lee et al., 2006). The PCR product generated from PA14Cas1_FWD caccatggacgacatttctcccag (SEQ ID NO:23) and PA14Cas1_REV ttatcatgcggatactgtgctc (SEQ ID NO:24) was cloned into pENTR™/TEV/D-TOPO using the Gateway system (Invitrogen). The cas1 sequence was confirmed by DNA sequencing and then recombined into a Gateway compatible expression vector (pHMGWA) containing an N-terminal His6MBP tag. The His6MBP-Cas1 fusion protein was expressed in BL21(DE3) cells that were induced with 0.5 mM isopropyl-β-D-thiogalactopyranoside (IPTG) at $OD_{600}$=0.5 in overnight cultures grown at 16° C. Cells from the overnight expression cultures were harvested by centrifugation (10,000×g) for 20 minutes. The cell pellet was resuspended in lysis buffer (20 mM imidazole, 0.01% Triton X-100, 100 u/ml DNaseI, 2 mM Tris(2-carboxyethyl) phosphine hydrochloride (TCEP), 0.5 mM phenylmethylsulfonyl fluoride (PMSF), protease inhibitors, 10% glycerol) and the slurry was sonicated on ice for 2 min in 10 second bursts. The lysate was clarified by centrifugation (22,000×g for 20 min) and the His6MBP-Cas1 fusion protein was bound to Ni-NTA affinity resin in batch (Qiagen). His6MBP-Cas1 was eluted from the resin in 50 ml lysis buffer containing 300 mM imidazole. The eluted protein was dialyzed at 4° C. overnight against gel filtration buffer (20 mM HEPES pH 7.5, 500 mM KCl, 1 mM Tris(2-carboxyethyl)phosphine hydrochloride (TCEP), 5% Glycerol) in the presence of tobacco etch virus (TEV) protease to remove the N-terminal His6MBP tag. The protein was concentrated (Amicon) for further purification on tandem Superdex 75 (16/60) sizing columns. A similar strategy was used for the expression and purification of the selenomethionine-containing protein, with the only major exception being the expression media. Briefly, Escherichia coli BL21(DE3) transformed with the Cas1 expression construct (PaCas1/pHMGWA) were grown in M9 minimal media supplemented with ampicillin At an $OD_{600}$ of 0.5, the following amino acids were added to inhibit methionine biogenesis and to allow for selenomethionine incorporation (Leu, Ile, Val: 50 mg/L; Phe, Lys, Thr: 100 mg/L; Selenomethionine: 75 mg/L) (Vanduyne et al., 1993). IPTG (0.5 mM) was added 15 minutes later and the culture was maintained at 16° C. overnight. The purified protein was concentrated to 9 mg/ml in 20 mM HEPES pH 7.5, with 100 mM KCl, 1 mM TCEP and 5% Glycerol.

Crystallization, data collection and structure determination. Native crystals were grown at 18° C. by vapor diffusion in hanging drops composed of equal volumes of protein solution (16 mg/ml Cas1 in 20 mM HEPES pH 7.6, 100 mM KCl, 1 mM TECP, 5% glycerol) and reservoir solution (250 mM $CaCl_2$, 50 mM HEPES pH 7.6, 10% PEG8000). Optimized SeMet-containing crystals were grown at 18° C. by vapor diffusion in hanging drops composed of equal volumes of protein solution (12 mg/ml Cas1 in 20 mM HEPES pH 7.6, 100 mM KCL, 1 mM TECP, 5% glycerol) and reservoir solution (250 mM calcium acetate, 50 mM HEPES pH7.8, 6% PEG5000 MME). All crystals were cryo-protected by soaking in well solution supplemented with 30% glycerol for 15 seconds and then flash cooled in liquid nitrogen.

Diffraction data were collected at the Advanced Light Source (beamline 8.2.2), Lawrence Berkeley National Laboratory. Phases for the Cas1 structure were determined from a highly redundant single wavelength anomalous dispersion (SAD) data set collected at the Au L-III edge ($\lambda$=1.036652 Å) using native crystals soaked in 10 mM KAu(CN)2 for 10 minutes. Data with an I/sigma of greater than 2.0 was measured out to 3.0 Å resolution. Data were processed in space group P212121 using XDS (Kabsch, 1988; Kabsch, 1993). SOLVE (Terwilliger and Berendzen, 1999) was used to locate six gold atoms in the crystallographic asymmetric unit and to calculate initial phases.

Density modification and initial model building was performed using RESOLVE (Adams et al., 2002). A crude initial model was constructed by manually placing alpha helices using COOT (Emsley and Cowtan, 2004). The model was extended by automated model building using RESOLVE (Adams et al., 2002; Terwilliger, 2000, 2003) and Buccaneer (Cowtan, 2006) and completed by iterative rounds refinement and model building using Phenix refine (Afonine et al., 2005) and COOT (Emsley and Cowtan, 2004), respectively. The final model was refined against an isomorphous 2.17 Å data set measured from selenomethionine-containing crystals, yielding a $R_{cryst}$ of 20.3% and $R_{free}$ of 25.8%.

To locate the metal binding site in Cas1, SeMet-containing Cas1 crystals (grown from 250 mM calcium chloride, 50 mM HEPES pH 7.8, 12% PEG5000 MME) were soaked in 5 mM $MnCl_2$ for two hours. Diffraction data was measured at the K absorption edge (1.8842 Å). Manganese ions were included in the refinement using elbow (http followed by ://www. followed by phenix-online org/ followed by documentation/ followed by elbow. followed by htm).

Activity assays. Purified recombinant Cas1 from PA14 (15.3 μM) was incubated at 25° C. with 1 μg of the indicated nucleic acid substrate (0.05 μM dsDNA, 0.05 μM ssDNA, 0.3 μM dsRNA and 0.6 μM sRNA) in the presence of 20 mM HEPES pH 7.5 and 100 mM KCl at 25° C. for 90 minutes. Each reaction was supplemented with no metal (NM) or with 2.5 mM magnesium ($Mg^{2+}$), manganese ($Mn^{2+}$), cobalt ($Co^{2+}$), calcium ($Ca^{2+}$), iron ($Fe^{3+}$), zinc ($Zn^{2+}$), or EDTA, as indicated. RNA substrates were generated by in vitro transcription of the first 10 repeats and nine spacers of CRISPR2 cloned into the plasmid vector pUC19. In vitro transcripts from both strands of CRISPR2 were generated using T7 RNA polymerase at 37° C. for 2-5 hrs, in a reaction including: 30 mM Tris pH 8.4, 25 mM $MgCl_2$, 5 mM of each nucleotide tri-phosphate, 10 mM Trition X-100, 10 mM dithiothreitol (DTT), 2 mM spermidine, 200 nM linearized dsDNA template (CRISPR2-pUC19). Transcripts were purified on denaturing polyacrylamide gels. Double-stranded CRISPR2 RNA substrates were generated by annealing the forward and reverse transcripts at 65° C. for 10 minutes. All nuclease assays were performed at 25° C.

ACCESSION NUMBERS. Refined models and experimental structure factors for the Cas1 protein from *P. aeruginosa* (PaCas1) have been deposited in the Protein Data Bank under accession number 3GOD.

Example 1

Identification of the *P. aeruginosa* PA14 cas1 Gene

*P. aeruginosa*, a gram-negative bacterium, is an opportunistic human pathogen known for its ability to grow in low-oxygen environments including the tissues of immunocompromised or cystic fibrosis patients. To investigate the function of the Cas1 protein, CRISPR elements in the genome of *Pseudomonas aeruginosa*, strain 14 (PA14) (Lee et al., 2006) were focused upon. Using a CRISPR-finding algorithm, two repetitive genetic elements with the distinct repeat-spacer-repeat architecture characteristic of CRISPRs have been identified in the PA14 genome (Grissa et al., 2007). These two elements flank a cassette of six open reading frames (ORFs) that are annotated as hypothetical proteins. Blast analysis (basic local alignment search tool) identified each of these ORFs (PA14_33300-33350) as CRISPR-associated (cas) genes (Altschul et al., 1997; Zegans et al., 2008).

Based on phylogenetic comparisons, seven distinct versions of the CRISPR-associated immune system have been identified (CASS1-7) (Makarova et al., 2006). The identity and genomic arrangement of the PA14 cas genes are characteristic of CASS3. Blast analysis of the predicted protein sequence for PA14 cas gene 33350 identified homologous sequences most typically annotated as Cas1 (COG1518). Cas1, a ~36 kD protein, has no obvious homology to proteins of known function. Due to its conservation across CRISPR systems, a molecular structure and function for the Cas1 protein from PA14 was determined.

Example 2

Crystal Structure of Cas1 Revealed a Novel Fold

The cas1 gene from *P. aeruginosa* was cloned and overexpressed in *E. coli*. The purified protein was crystallized by vapor diffusion in hanging drops with a PEG-salt precipitant. The Cas1 structure was solved by SAD (single-wavelength anomalous dispersion) using a gold derivative and the final structure was refined against a 2.17 Å data set, yielding an $R_{cryst}$ of 20.3% and an $R_{free}$ of 25.8%.

The Cas1 protein has a novel three-dimensional fold consisting of two structurally distinct domains (FIG. 1). The N-terminal β-strand domain includes residues 1-106 and is composed of 10 β-strands and two α-helices (yellow). This β-strand domain is connected to a C-terminal α-helical domain by a flexible linker (residues 107-112, green). The α-helical domain, including residues 113-324, comprises 10 α-helices (gray). Conserved residues are colored red. Side chains of the four universally conserved residues (E190, N223, H254, and D265), as well a strongly conserved aspartic acid at position 268 (D or E) are displayed as sticks were oxygen's are red, nitrogen's are blue and carbons are gray. Residues E190, H254 and D268 coordinate a manganese ion (green sphere). All ribbon diagrams were prepared using PYMOL (DeLano, 2002).

Figure 2:
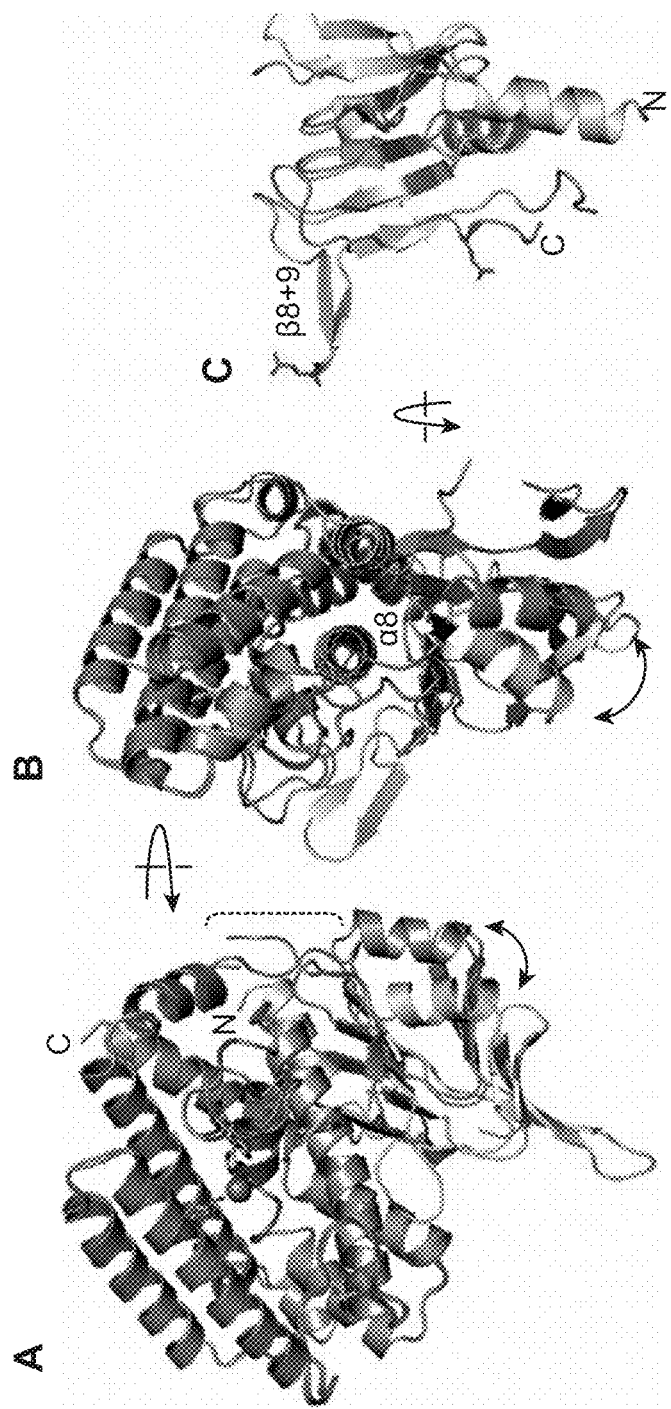
FIGS. 2A-C depict two different orientations and two distinct folds in the β-strand domain of Cas1 from *P. aeruginosa*. Panel A depicts superimposition of the C-terminal α-helical domains of molecules A and C. Panel B depicts a view down the barrel of α8. Panel C illustrates that superimposing the β-strand domains for molecule A and C highlights two structural differences.

Comparison of the four Cas1 molecules (A-D) in the asymmetric unit of the crystal shows that their α-helical domains are nearly identical with an average root mean square deviation (r.m.s.d.) for equivalently positioned Cα atoms between residues 113-324 of 0.32 Å. There are, however, substantial differences in the fold and orientation of the β-strand domains (FIG. 2). Thus, the linker connecting the α and β domains serves as a hinge that allows the two domains of a single molecule to be positioned in different relative orientations (FIG. 2 Panels A and B). FIG. 2, Panel shows that the C-terminal α-helical domains of molecules A and C superimpose (residues 113-321) with an average r.m.s.d of 0.40 Å. The β-strand domains of these two molecules are in different orientations (two-way arrow) with respect to their α-helical domains. Coloring of molecule A is consistent with that in FIG. 1. Molecule C is colored light blue, with conserved residues colored pink. The α-helical and β-strand domains of molecules A and B are in the same relative orientation and the two molecules superimpose with an average r.m.s.d. of 0.20 Å for 318 equivalent Cα positions between residues 4-321. Molecules C and D are similar to one-another (0.57 Å Cα r.m.s.d.), but distinct from A and B. FIG. 2, Panel B shows a view down the barrel of α8 after rotation of 90° about the Y-axis and 20° about the X-axis. Pronounced structural differences occur at the N-terminus and in the positions of β-strands 8 and 9 (FIG. 2, Panel C). Molecules A and B have a well-ordered N-terminal α-helix (residues 6-16), whereas this region is disordered in molecule C. The N-terminus of molecule D forms an extended coil that is oriented in the opposite direction from that observed in molecules A and B; this coil forms crystal contacts with β-strands 3 and 4 (residues 36-52) in molecule C. In FIG. 2, panel C the superimposed β-strand domains are rotated 90° about the X-axis and viewed from the perspective of the α-helical domain. β-strands 8 and 9 form a short anti-parallel β-sheet in molecule A. This feature is not observed in molecule C, instead the sequence that would be part of β-strand 9 forms part of the unordered linker Glutamate 96 (teal sticks) relates the primary sequence of both molecules to secondary structure elements in this region.

Figure 3:
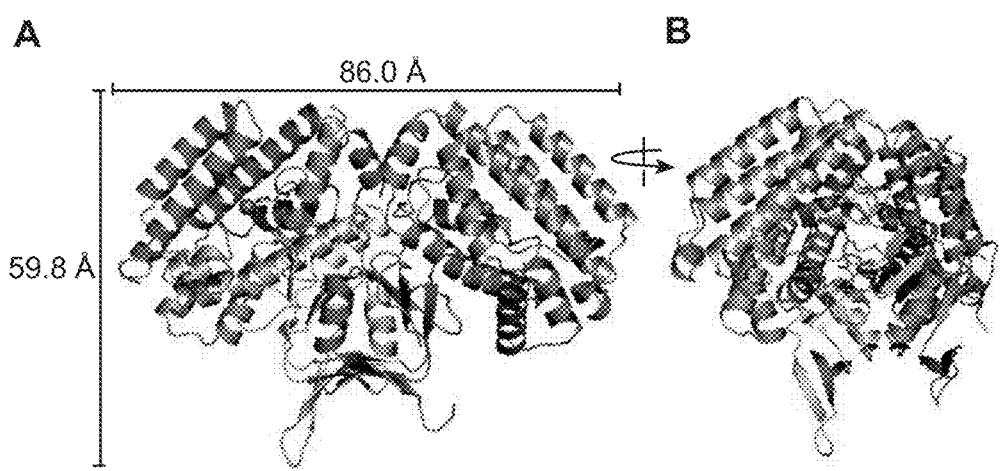
FIGS. 3A and B depict dimerization of the Cas1 protein from *P. aeruginosa*. Panel A depicts a ribbon diagram of Cas1 homodimer with molecule A shown in grey and molecule C shown in light blue. Panel B shows a view down the dimer interface.

Cas1 molecules with different β-strand domain structures form dimers in the asymmetric unit of the crystal, yielding A-C and B-D homodimers. The Cas1 homodimer is shaped like a butterfly, where the α-helical and β-strand domains of each molecule represent the upper and lower lobe of each 'wing' (FIG. 3). The wingspan of the Cas1 homodimer is ~86 Å, and each wing stands ~60 Å from top to bottom and ~46 Å thick. The two molecules in each dimer are related by a pseudo-two-fold axis of symmetry centered about the dimer interface. Extensive hydrogen bonding and two salt bridges (C/Glu96-A/His248; C/Asp98-A/Arg259) at the dimer interface result in 1,761 Å2 of buried surface area. Notably, the dimer is maintained in high salt (500 mM) buffers and elutes from a calibrated Superdex S-75 size exclusion column with a retention volume consistent with a protein of ~84 kDa, suggesting that Cas1 (~36 kDa) is homodimeric in solution. FIG. 3, Panel A shows conserved residues colored red in molecule A and pink in molecule C, side chains of the four universally conserved residues displayed as sticks, two of the four universally conserved residues (Glu190 and His254) and a well conserved aspartic acid at position 268 (Asp or Glu) coordinate a manganese ion (green sphere). FIG. 3, Panel B provides a look down the dimer interface after sixty-degree rotation about the Y-axis.

Structural comparisons performed using the DALI (Holm and Sander, 1993) and VAST (Gibrat et al., 1996) servers reveal a structural homolog of the Cas1 protein. The Cas1 structure from *P. aeruginosa* (PaCas1) is most similar (Z-score 17.5) to the unpublished structure of a hypothetical protein from *Aquifex aeolicus* (pdb id:2YZS). The amino acid sequences of these two proteins are highly divergent (17.6% identity, 37.0% similarity) and are not recognized as homologs by BlastP (Altschul et al., 1997). However, further examination of the *A. aeolicus* protein (gene ID: 1193018) using PSI-Blast and genomic neighborhood analysis reveals that this is a Cas1 protein flanked by cas genes that are most similar to those of the CASS7 subtype.

Figure 4:
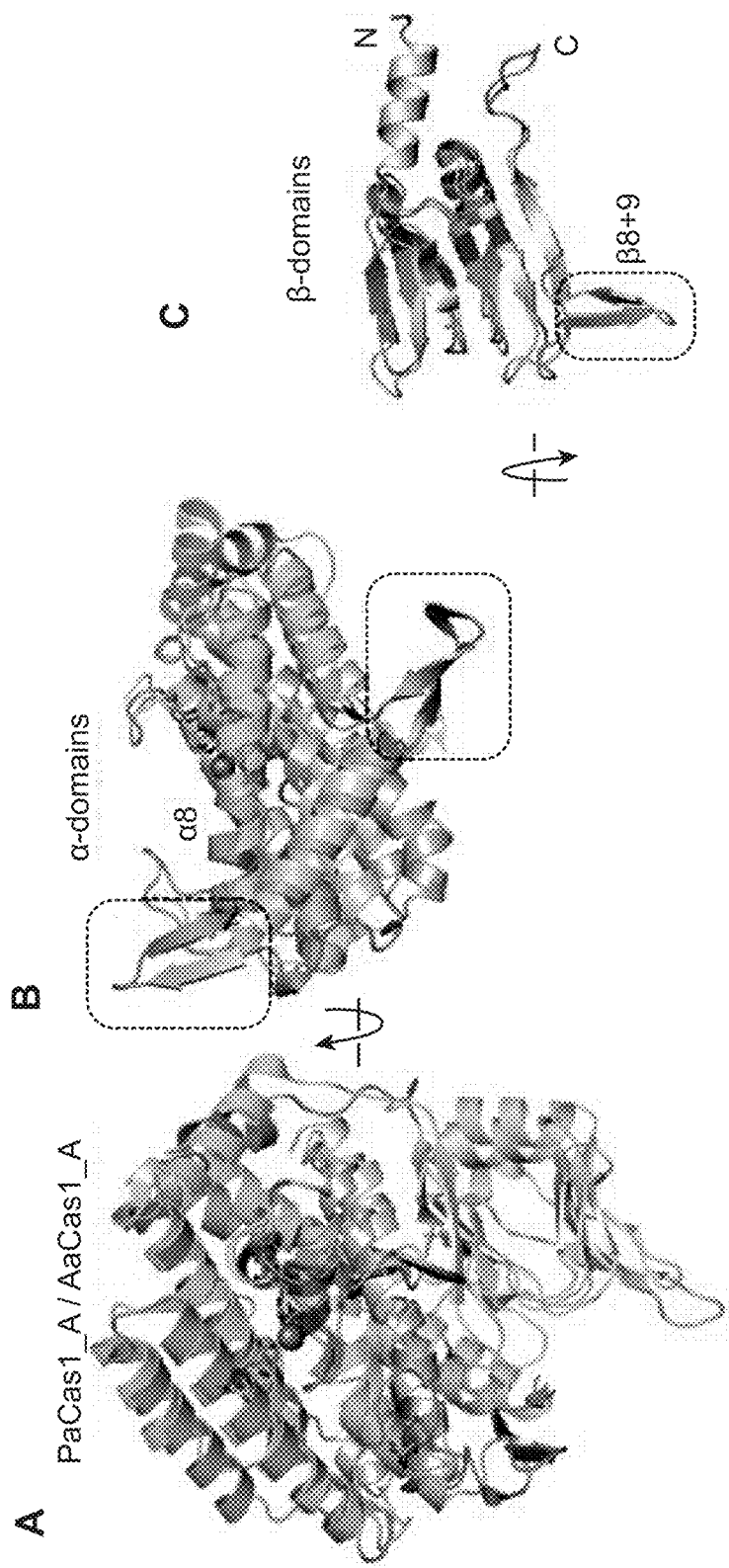
FIGS. 4A-C provide a schematic of the structural comparison of the Cas1 proteins from *P. aeruginosa* and *A. aeolicus*. Panel A shows molecule A from PaCas1 (in grey) superimposed on molecule A from AaCas1 (light green). Panel B depict superposition of the α-helical domains of PaCas1 and AaCas1, as viewed from the perspective of the β-strand domain. Panel C depict the β-strand domains of these two molecules.
Figure 8:
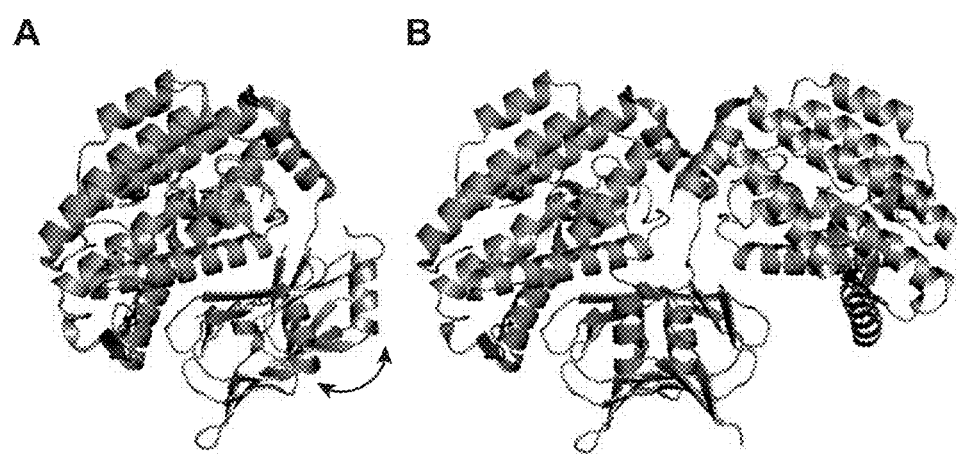
FIGS. 8A and 8B depict Cas1 protein structure from *A. aeolicus*. Panel A shows the superimposition of molecules A (green) and B (pink) of AaCas1. Panel B shows a dimer formed from molecules A (green) and B (pink) of AaCas1.

The Cas1 protein from *A. aeolicus* (AaCas1) shares a similar tertiary and quaternary architecture to the Cas1 protein structure from *P. aeruginosa* (FIG. 4, Panel A; FIG. 8). FIG. 4, Panel A shows that the α-helical domains of molecule A from PaCas1 (PaCas1_A) and molecule A from AaCas1 (AaCas1_A) share 91 equivalent Cα positions that superimpose with an average r.m.s.d of 1.28 Å. The color scheme of PaCas1 is consistent with that in FIG. 1. AaCas1 is colored light green and conserved residues are colored pink Similar to the PaCas1 protein, the AaCas1 is a dimer composed of two molecules with β-domains in distinct orientations, despite having been crystallized under different conditions and in a different space group. FIG. 4, Panel B depicts that superposition of the α-helical domains of PaCas1 and AaCas1, as viewed from the perspective of the β-strand domain, highlights two structural differences. The two loops that connect α-helices 10 to 11 and 11 to 12 in PaCas1 are each replaced by two finger-like projections in the AaCas1 structure (gray boxes). Alpha-helix 8 (α8) of PaCas1 is positioned horizontally along the top and the two molecules are displayed at a 90° rotation about the Y-axis. FIG. 4, Panel C illustrates that the β-strand domains of these two molecules share 35 equivalent Cα atoms that superimpose with an average r.m.s.d of 1.21 Å. These two molecules are displayed from the perspective of the α-helical domain. β-strands 8 and 9 (gray box) are flipped out of the β-strand domain in molecule A of PaCas1 and positioned adjacent to α8 (FIG. 4, Panel A). Comparison of molecule A from PaCas1 (PaCas1_A) and molecule A from AaCas1 (AaCas1_A) reveals two prominent structural differences in the α-helical domain (FIG. 4, Panel B). The two short loops that connect α-helix 10 to 11 and 11 to 12 in PaCas1 are each replaced by finger-like projections consisting of two antiparallel β-strands (residues 238-255 and 273-286, respectively) in the AaCas1 structure.

These two Cas1 structures do not share detectable homology with any other protein structure currently deposited in the protein data bank (PDB).

Example 3

Cas1 Contains a Conserved Divalent Metal Ion Binding Site

To investigate whether Cas1 includes a divalent metal ion binding site(s), crystals of the selenomethionine-substituted PaCas1 protein were soaked in solutions containing manganese chloride and diffraction data at the K absorption edge was measured. Anomalous difference electron density maps contoured at five sigma revealed eight unique peaks, three of which correspond to manganese ions (Mn) in molecules A, B and C, while signal from the other five peaks are from selenomethionines. Each of these Mn ions, as well as an additional Mn ion in molecule D (visible at four sigma), are located in equivalent positions in the α-helical domains of each molecule and are coordinated by three conserved residues (Glu190, His254 and Asp286) (FIG. 1). Although the three-dimensional fold of Cas1 is unique, the residues coordinating the Mn ion are typical among nucleases that employ one or more metals in their active site. In fact, the chemical environment of the Cas1 metal binding site is remarkably similar to the active site of the manganese specific endonuclease domain from the cap-snatching subunit of the influenza polymerase (Dias et al., 2009).

Although no metal ions were included in the AaCas1 structure, residues E143, H206 and E221 are located in equivalent positions to the metal binding residues in the PaCas1 structure (FIGS. 8 and 9). The conservation of these residues in Cas1 sequences from diverse CASS subfamilies, as well as their conserved three-dimensional arrangement in the AaCas1 and PaCas1 structures, suggests a common role for these residues in coordinating a metal ion.

Example 4

Cas1 is a Metal-dependent DNA-Specific Endonuclease

Figure 5:
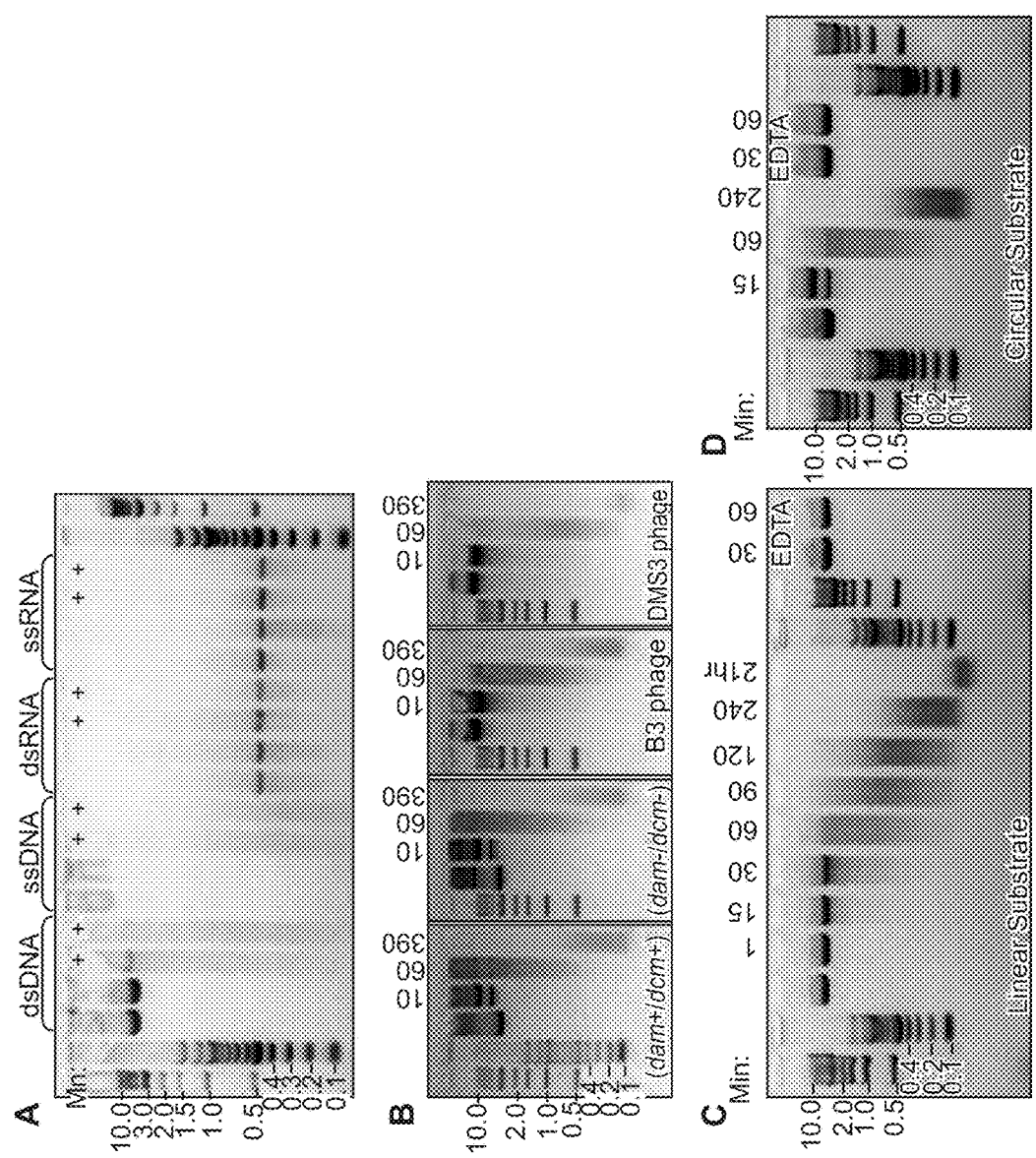
FIGS. 5A-D illustrate that Cas1 is a DNA-specific endonuclease. Panel A shows that Cas1 nuclease activity is restricted to DNA substrates. Panel B depicts the time course of Cas1 nuclease activity on four distinct dsDNA substrates. Panel C depicts the time course of Cas1 nuclease activity on linear dsDNA substrate. Panel D illustrates that Cas1 is an endonuclease.

Cas1 nuclease activity was tested by adding PaCas1 to a variety of nucleic acid substrates including: linear and circular double-stranded DNA (dsDNA: CRISPR2 cloned into pUC19), circular single-stranded DNA (ssDNA: M13 phage), linear double-stranded RNA (dsRNA; in vitro transcript of CRISPR2) and linear single-stranded RNA (ssRNA; in vitro transcript of CRISPR2). Cas1 is a metal-dependent DNA-specific endonuclease (FIG. 5). FIG. 5, Panel A depicts that Cas1 nuclease activity is restricted to DNA substrates. Lanes 1 and 2 are 1 kb and 100 bp DNA ladders, respectively. Lanes 3-6 are dsDNA, lanes 7-10 are ssDNA, lanes 11-14 are dsRNA and lanes 15-18 are ssRNA. The first lane of each substrate type is nucleic acid alone, followed by a lane with nucleic acid and Cas1 in a no metal buffer. The last two lanes of each substrate type include nucleic acid, Cas1 and 2.5 mM $Mn^{2+}$. The last lane of each substrate type was phenol extracted prior to electrophoresis. The dsDNA substrate is CRISPR2 from PA14 cloned into pUC19 (pUC19-C2) and linearized with KpnI (4 Kb). The ssDNA substrate is from M13 phage (reference sequence: NC_003287, 6407 nt). RNA substrates are from in vitro transcripts of the first 10 repeats and 9 spacers of CRISPR2 (568 nt). All reactions were incubated at 25° C. for 90 minutes prior to electrophoresis on a 1.5% agarose gel. Metal-dependent nuclease activity of Cas1 is independent of both sequence and methylation (dam/dcm) pattern (FIG. 5, Panel B). FIG. 5, Panel B shows time course of Cas1 nuclease activity on four distinct dsDNA substrates. Lanes 1 and 2 are 1 kb and 100 bp DNA ladders, respectively. The 1 kb ladder is the first lane of each of three subsequent panels. The first panel is pUC19-C2 DNA from isolated from methyltransferases (dam+/dcm+) component *E. coli* and the second panel is pUC19-C2 DNA from methyltransferases delete (dam−/dcm−) *E. coli*. The third and fourth panels are B3 and DMS3 phage DNA (respectively); each isolated from *P. aeruginosa* (PA14). The lanes for each substrate types are: nucleic acid alone, followed by 10, 60 and 390 minute incubations with Cas1 in a reaction buffer containing 2.5 mM $Mn^{2+}$. The non-sequence specific nuclease activity of Cas1 on circular and linear DNA substrates isolated from *E. coli* or from *P. aeruginosa* results in reaction products that migrate as a non-specific smear on agarose gels (FIG. 5, Panels B, C and D). The average molecular weight of the DNA cleavage products continually decreases over time, resulting in a minimal cleavage product of approximately 80 base pairs in overnight reactions (FIG. 5, Panel C). FIG. 5, Panel C illustrates the time course of Cas1 nuclease activity on linear dsDNA substrate. Lanes 1 and 2 are 1 kb and 100 bp DNA ladders, respectively. Lane 3 is linearized dsDNA alone. Cas1 mediated nuclease reactions (lanes 4-11) were phenol extracted at 1, 15, 30, 60, 90, 120, 240 minutes and at 21 hours, prior to electrophoresis. The Cas1 time course is followed by the 100 bp and 1 kb DNA ladders, respectively. Cas1 mediated nuclease activity is inhibited by EDTA in the last two lanes (30 and 60 minute time points). FIG. 5, Panel D illustrates that Cas1 is an endonuclease. Lanes 1 and 2 are 1 kb and 100 bp DNA ladders, respectively. Lane 3 is circular dsDNA alone (CRISPR2 from PA14 cloned into pUC19). Cas1 mediated nuclease reactions (lanes 4-6) were phenol extracted at 15, 60, 240 minutes prior to electrophoresis. Endonuclease activity of Cas1 is inhibited by EDTA (lanes 7-6). The last two lanes are 100 bp and 1 kb DNA ladders respectively.

Figure 6:
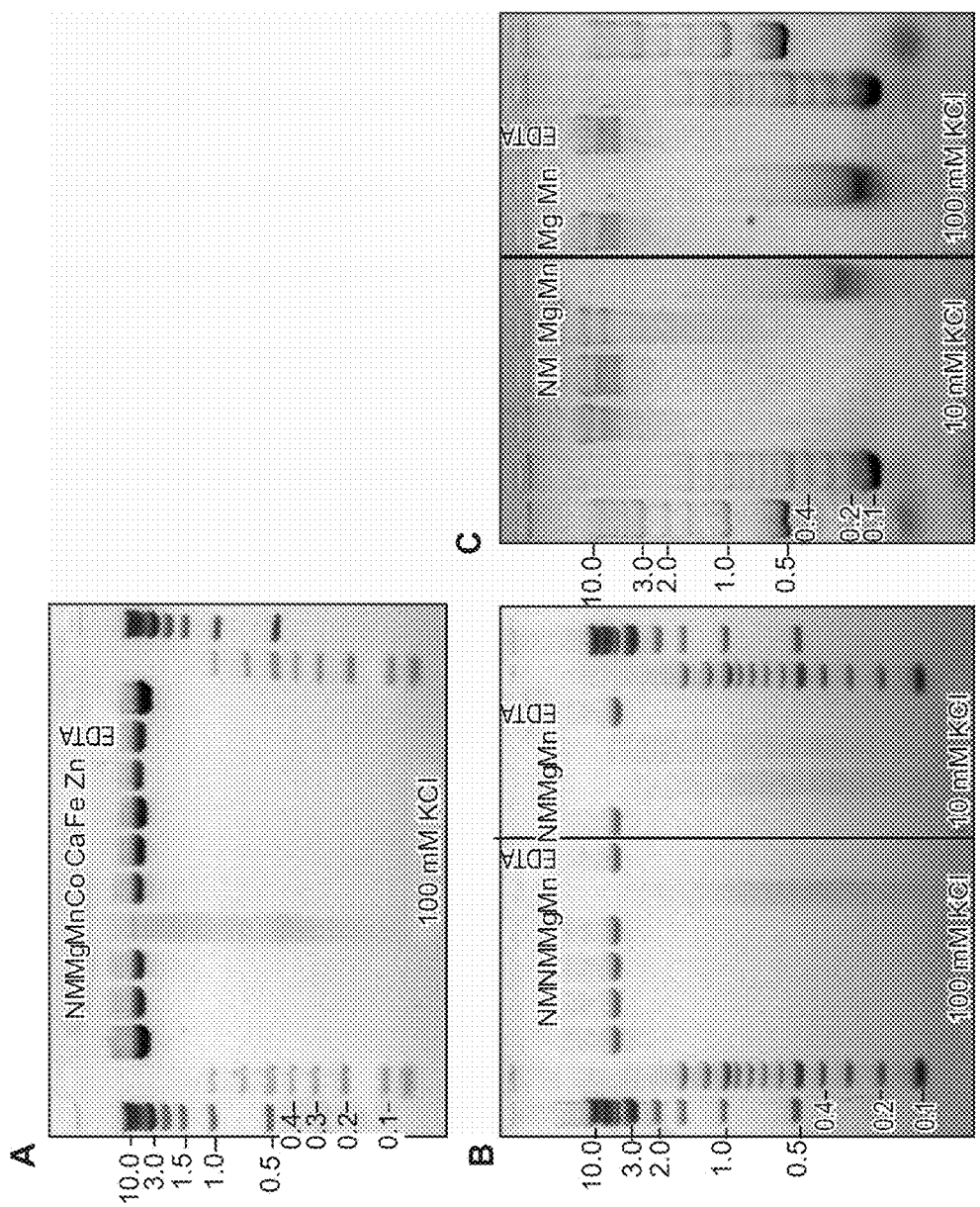
FIGS. 6A-C illustrate that Cas1 is a metal-dependent nuclease. Panel A illustrates that manganese supports Cas1 mediated non-specific nuclease activity. Panel B shows that the metal preference of Cas1 is salt dependent. Panel C shows that Cas1 mediated cleavage of ssDNA is supported exclusively by manganese.

Metal ion substitution is a common strategy for understanding the role of the metal ions in metallonucleases. A panel of metal ion cofactors including alkaline earth metals and transition metals that are commonly found in association with metal dependent nucleases were tested for their ability to support Cas1 mediated nuclease activity on dsDNA substrates. In FIG. 6, Panel A, lanes 1 and 2 are 1 kb and 100 bp DNA ladders, respectively. Lane 3 is linear dsDNA alone (CRISPR2 from PA14 cloned into pUC19 and linearized with KpnI). Nuclease reactions (lanes 4-9) were performed in 100 mM KCl and 20 mM HEPES pH7.5 at 25° C. for 90 minutes. Each reaction was supplemented with no metal (NM) or with 2.5 mM magnesium ($Mg^{2+}$), manganese ($Mn^{2+}$), cobalt ($Co^{2+}$), calcium ($Ca^{2+}$), iron ($Fe^{3+}$), zinc ($Zn^{2+}$), or EDTA, respectively. Lane 12 is linear dsDNA alone. Lanes 13 and 14 are 100 bp and 1 kb DNA ladders, respectively. All reactions were phenol extracted prior to electrophoresis on a 1.5% agarose gel. Only magnesium ($Mg^{2+}$) and manganese ($Mn^{2+}$) support Cas1-mediated cleavage of dsDNA, and metal preference is dependent on monovalent salt concentrations (FIG. 6, Panels A and B). In FIG. 6, Panel B lanes 1 and 2 are 1 kb and 100 bp DNA ladders, respectively. Lane 3 is linear dsDNA alone. Lane 4 is linear dsDNA in 100 mM KCl and 20 mM HEPES pH7.5. Lanes 5-12 all include Cas1 and linear dsDNA in a 100 mM KCl or 10 mM KCl reaction buffer supplemented with no metal (NM) or with 2.5 mM magnesium ($Mg^{2+}$), manganese ($Mn^{2+}$) or EDTA, respectively. Lanes 13 and 14 are 100 bp and 1 kb DNA ladders, respectively. Although most nucleases exhibit highest activity in the presence of Mg, Cas1 is more active with $Mn^{2+}$ than with $Mg^{2+}$ at physiological KCl concentrations (FIG. 6, Panel B). Furthermore, Cas1-mediated cleavage of ssDNA, is supported exclusively by $Mn^{2+}$, regardless of KCl concentration (FIG. 6, Panel C). In FIG. 6, Panel C lanes 1 and 2 are 1 kb and 100 bp DNA ladders, respectively. Lane 3 is linear ssDNA alone (M13 circular single-stranded DNA). Lanes 4-9 all include Cas1 and ssDNA in a 10 mM KCl or 100 mM KCl reaction buffer supplemented with no metal (NM) or with 2.5 mM magnesium ($Mg^{2+}$), manganese ($Mn^{2+}$) or EDTA, as indicated. Lanes 10 and 11 are 100 bp and 1 kb DNA ladders, respectively.

Figure 7:
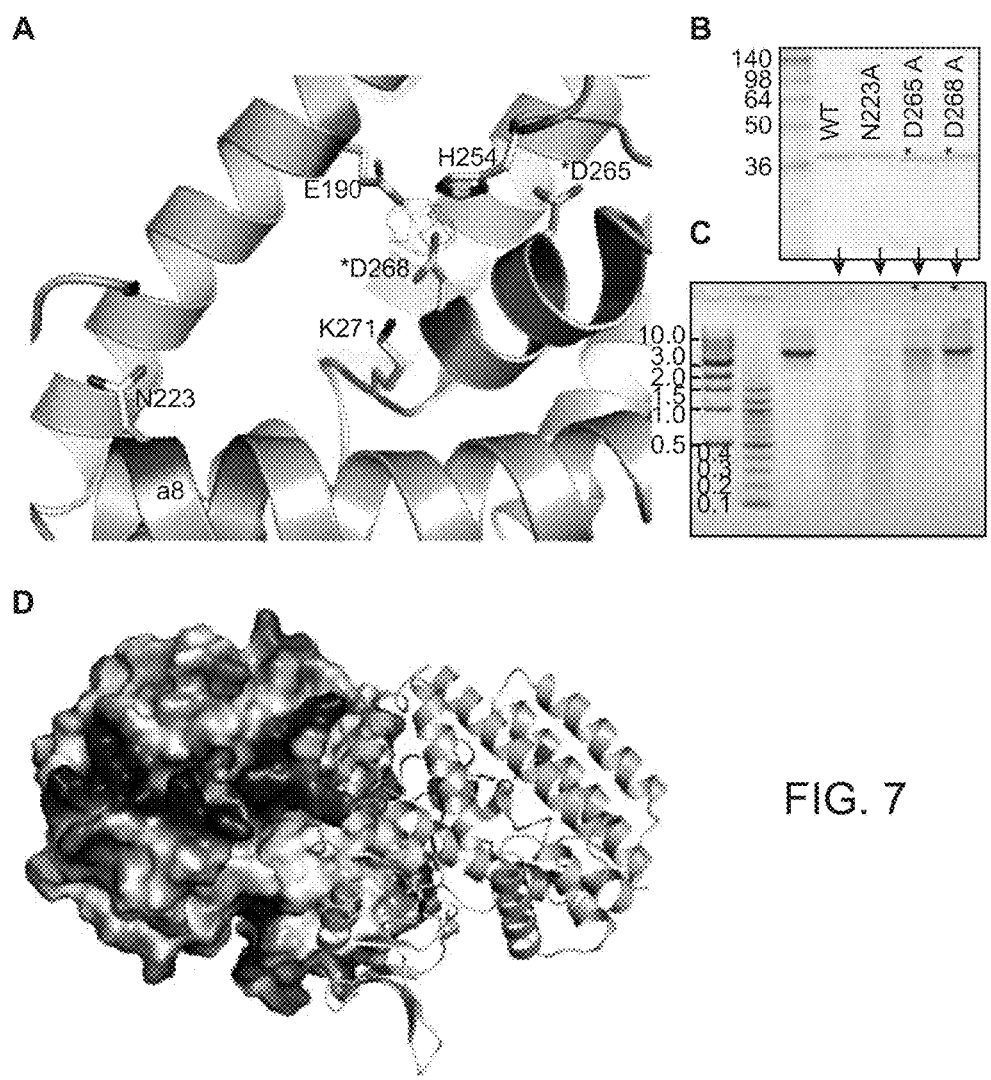
FIGS. 7A-D illustrate that mutants of conserved residues in the metal binding pocket of Cas1 inhibit nuclease activity. Panel A shows a close-up of the metal binding pocket in the α-helical domain of molecule A. Panel B shows SDS-PAGE of the purified Cas1 and Cas1 mutants. Panel C depicts nuclease activity assay for Cas1 and Cas1 mutants.

A series of mutants were constructed to investigate the role of conserved residues clustered in or around the Cas1 metal-binding pocket. Residues E190, N223, H254, D265 and D268 were mutated to alanine (FIG. 7, Panel A). Although each of these mutants was over-expressed, mutation of either E190 or H254 resulted in reduced stability of the protein and we were unable to purify these two point mutants to homogeneity (FIG. 7B). The nuclease activity of the three stable mutants (N223A, D265A and D268A) was tested.

FIG. 7, Panel A shows a close-up of the metal binding pocket in the α-helical domain of molecule A. Anomalous difference electron density maps contoured at 5 sigma reveal a manganese ions (green mesh), coordinated by E190, H254 and D268. Asparagine 223 is one of only four universally conserved residues and is the only strictly conserved residue located outside the metal binding pocket (FIG. 7, Panel A). Asparagine 223 is located at the N-terminal end of α-helix 8, 15.5 Å away from the metal ion. An alanine substitution at this position (N223A) results in a modest reduction in non-specific nuclease activity (FIG. 7, Panel C). This is in contrast to the potent inhibition of nuclease activity observed in mutations made within the metal binding pocket. Mutation of acidic residues in the metal binding pocket at position 265 (D265A) or at metal coordinating residue 268 (D268A), inhibits non-specific nuclease activity. In FIG. 7, Panel C, the first two lanes are 1 kb and 100 bp DNA ladders, respectively. Lane 3 is dsDNA alone, lanes 4-7 include dsDNA, 2.5 mM $Mn^{2+}$ and one of the following Cas1 proteins in order: wild type Cas1, N223A, D265A and D268A. All reactions were performed at 25° C. for 90 minutes prior to phenol extraction. Samples were resolved by electrophoresis on a 1.5% agarose gel and stained with ethidium bromide. (*) denotes metal binding mutants that inhibit non-specific nuclease activity. In FIG. 7, Panel D the two subunits of the Cas1 (A-C) homodimer from *P. aeruginosa* (PA14) are displayed as a charge smoothed surface potential (molecule C) and a ribbon diagram of (molecule A). Basic residues (blue) cluster around the acidic metal binding pocket (red) creating a positive surface potential that may serve to position nucleic acid substrates in proximity to the metal binding site. The Cas1 homodimer is rotated 180° about the Y-axis with respect to the orientation in FIG. 3.

Thus three independent methods, metal chelation, metal ion substitution or mutation of metal coordinating residues, all suggest that the metal ion is critical for the non-specific degradation of DNA (FIGS. 5, 6 and 7, respectively).

The metal ion is located on one exposed face of the α-helical domain. An extensive cluster of basic residues including R192, K195, R196, K199, R212, K214, R215, K256 R258, R259 and K271 form a positively charged surface that spans this face of the α-helical domain and may serve to position nucleic acid substrate near this metal ion (FIG. 7, Panel D).

Example 5

Identification of a Cas1 Protein Structure from *Aquifex aeolicus*

FIG. 8, Panel A shows that the Cas1 protein structure from *A. aeolicus* (AaCas1) consists of two domains, an N-terminal β-strand domain (residues 2-77) and a C-terminal α-helical domain (88-316). The N and C-terminal domains are connected by a linker (77-83) that allows the two domains to sample different relative orientation. Superimposing residues 88-316 from the α-helical domains of molecules A (green) and B (pink) of AaCas1 (0.59 Å Cα r.m.s.d), reveals differences in domain positioning between these two molecules. FIG. 8, Panel B shows that two molecules with α-helical and β-strand domains in different orientations form a dimer. The dimer interface is mediated by hydrogen bonding between β-strand domains and results in 1,439 Å$^2$ of buried surface area. Conserved residues are yellow and the side chains of universally conserved residues are displayed as sticks with the atoms in each of these side chains colored according to red=oxygen, nitrogen=blue and carbon=gray. The coordinates for this structure were deposited by Ebihara, A., Yokoyama, S., and Kuramitsu, S. on Jul. 6, 2007 (PDB: 2YZS).

Example 6

Cas1 Sequences are Diverse

FIG. 9 depicts an alignment of Cas1 sequences from each of the 7 major CASS subclasses. Theses sequences were aligned by Mcoffee (http:// followed by www. followed by tcoffee. followed by org/). Twenty-one sequences, 3 from each of the 7 major CASS subfamilies, are labeled by a two letter abbreviation of the genus and species, followed by 'Cas1', the NCBI gene identification number and the CASS subfamily number 1-7, previously assigned by Makarova et al (2006) (e.g. *Pseudomonas aeruginosa, Cas*1, NCBI gene identification number: 4380485, from the CASS subfamily 3 is abbreviated as, "PaCas1_4380485_CASS3"). Universally conserved residues are in red columns and well-conserved residues are in yellow columns.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002). PHENIX: building new software for automated crystallographic structure determination. Acta Crystallographica Section D-Biological Crystallography 58, 1948-1954.

Afonine, P. V., Grosse-Kunstleve, R. W., and Adams, P. D. (2005). A robust bulk-solvent correction and anisotropic scaling procedure. Acta Crystallographica Section D-Biological Crystallography 61, 850-855.

Agari, Y., Yokoyama, S., Kuramitsu, S., and Shinkai, A. (2008). X-ray crystal structure of a CRISPR associated protein, Cse2, from *Thermus thermophilus* HB8. Proteins-Structure Function and Bioinformatics, 1063-1067.

Altschul, S. F., Madden, T. L., Schaffer, A. A., Zhang, J. H., Zhang, Z., Miller, W., and Lipman, D. J. (1997). Gapped BLAST and PSI-BLAST: a new generation of protein database search programs. Nucleic Acids Research 25, 3389-3402.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Beloglazova, N., Brown, G., Zimmerman, M. D., Proudfoot, M., Makarova, K. S., Kudritska, M., Kochinyan, S., Wang, S., Chruszcz, M., Minor, W., et al. (2008). A novel family of sequence-specific endoribonucleases associated with the clustered regularly interspaced short palindromic repeats. Journal of Biological Chemistry 283, 20361-20371.

Bolotin, A., Ouinquis, B., Sorokin, A., and Ehrlich, S. D. (2005). Clustered regularly interspaced short palindrome repeats (CRISPRs) have spacers of extrachromosomal origin. Microbiology-Sgm 151, 2551-2561.

Brouns, S. J., Jore, M. M., Lundgren, M., Westra, E. R., Slijkhuis, R. J., Snijders, A. P., Dickman, M. J., Makarova, K. S., Koonin, E. V., and van der Oost, J. (2008). Small CRISPR RNAs guide antiviral defense in prokaryotes. Science 321, 960-964.

Busso, D., Delagoutte-Busso, B., and Moras, D. (2005). Construction of a set Gateway-based destination vectors for high-throughput cloning and expression screening in *Escherichia coli*. Analytical Biochemistry 343, 313-321.

Carte, J., Wang, R., Li, H., Terns, R. M., and Terns, M. P. (2008). Cas6 is an endoribonuclease that generates guide RNAs for invader defense in prokaryotes. Genes and Development 22, 3489-3496.

Cowtan, K. (2006). The Buccaneer software for automated model building. 1. Tracing protein chains. Acta Crystallographica Section D-Biological Crystallography 62, 1002-1011.

DeLano, W. L. (2002). The PyMOL Molecular Graphics System

Dias, A., Bouvier, D., Crepin, T., McCarthy, A. A., Hart, D. J., Baudin, F., Cusack, S., and Ruigrok, R. W. (2009). The cap-snatching endonuclease of influenza virus polymerase resides in the PA subunit. Nature.

Dupureur, C. M. (2008a). An Integrated Look at Metallonuclease Mechanism. Current Chemical Biology 2, 159-173.

Dupureur, C. M. (2008b). Roles of metal ions in nucleases. Curr Opin Chem Biol 12, 250-255.

Ebihara, A., Yao, M., Masui, R., Tanaka, I., Yokoyama, S., and Kuramitsu, S. (2006). Crystal structure of hypothetical protein TTHB192 from *Thermus thermophilus* HB8 reveals a new protein family with an RNA recognition motif-like domain. Protein Sci 15, 1494-1499.

Emsley, P., and Cowtan, K. (2004). Coot: model-building tools for molecular graphics. Acta Crystallographica Section D-Biological Crystallography 60, 2126-2132.

Gibrat, J. F., Madej, T., and Bryant, S. H. (1996). Surprising similarities in structure comparison. Curr Opin Struct Biol 6, 377-385.

Grissa, I., Vergnaud, G., and Pourcel, C. (2007). CRISPRFinder: a web tool to identify clustered regularly interspaced short palindromic repeats. Nucleic Acids Res 35, W52-57.

Haft, D. H., Selengut, J., Mongodin, E. F., and Nelson, K. E. (2005). A guild of 45 CRISPR-associated (Cas) protein families and multiple CRISPR/Cas subtypes exist in prokaryotic genomes. Plos Computational Biology 1, 474-483.

Holm, L., and Sander, C. (1993). Protein structure comparison by alignment of distance matrices. J Mol Biol 233, 123-138.

Jansen, R., van Embden, J. D. A., Gaastra, W., and Schouls, L. M. (2002). Identification of genes that are associated with DNA repeats in prokaryotes. Molecular Microbiology 43, 1565-1575.

Kabsch, W. (1988). AUTOMATIC INDEXING OF ROTATION DIFFRACTION PATTERNS J. Appl. Cryst. 21, 67-71.

Kabsch, W. (1993). Automatic Processing of Rotation Diffraction Data from Crystals of Initially Unknown Symmetry and Cell Constants. Journal of Applied Crystallography 26, 795-800.

Lee, D. G., Urbach, J. M., Wu, G., Liberati, N. T., Feinbaum, R. L., Miyata, S., Diggins, L. T., He, J., Saucier, M., Deziel, E., et al. (2006). Genomic analysis reveals that *Pseudomonas aeruginosa* virulence is combinatorial. Genome Biol 7, R90.

Makarova, K. S., Aravind, L., Grishin, N. V., Rogozin, I. B., and Koonin, E. V. (2002). A DNA repair system specific for thermophilic Archaea and bacteria predicted by genomic context analysis. Nucleic Acids Res 30, 482-496.

Makarova, K. S., Grishin, N. V., Shabalina, S. A., Wolf, Y. I., and Koonin, E. V. (2006). A putative RNA-interference-based immune system in prokaryotes: computational analysis of the predicted enzymatic machinery, functional analogies with eukaryotic RNAi, and hypothetical mechanisms of action. Biology Direct 1, 1-26.

Marraffini, L. A., and Sontheimer, E. J. (2008). CRISPR Interference Limits Horizontal Gene Transfer in Staphylococci by Targeting DNA. Science 322, 1843-1845.

Mojica, F. J., Diez-Villasenor, C., Soria, E., and Juez, G. (2000). Biological significance of a family of regularly spaced repeats in the genomes of Archaea, Bacteria and mitochondria. Mol Microbiol 36, 244-246.

Mojica, F. J. M., Diez-Villasenor, C., Garcia-Martinez, J., and Soria, E. (2005). Intervening sequences of regularly spaced prokaryotic repeats derive from foreign genetic elements. Journal of Molecular Evolution 60, 174-182.

Pourcel, C., Salvignol, G., and Vergnaud, G. (2005). CRISPR elements in *Yersinia pestis* acquire new repeats by preferential uptake of bacteriophage DNA, and provide additional tools for evolutionary studies. Microbiology-Sgm 151, 653-663.

Terwilliger, T. C. (2000). Maximum-likelihood density modification. Acta Crystallographica Section D-Biological Crystallography 56, 965-972.

Terwilliger, T. C. (2003). Automated main-chain model building by template matching and iterative fragment extension. Acta Crystallographica Section D-Biological Crystallography 59, 38-44.

Terwilliger, T. C., and Berendzen, J. (1999). Automated MAD and MIR structure solution. Acta Crystallographica Section D-Biological Crystallography 55, 849-861.

Vanduyne, G. D., Standaert, R. F., Karplus, P. A., Schreiber, S. L., and Clardy, J. (1993). Atomic Structures of the Human Immunophilin Fkbp-12 Complexes with Fk506 and Rapamycin. Journal of Molecular Biology 229, 105-124.

Yang, W. (2008). An equivalent metal ion in one- and two-metal-ion catalysis. Nature Structural & Molecular Biology 15, 1228-1231.

Zegans, M. E., Wagner, J. C., Cady, K. C., Murphy, D. M., Hammond, J. H., and O'Toole, G. A. (2008). Interaction between bacteriophage DMS3 and host CRISPR region inhibits group behaviors of *P. aeruginosa*. Journal of Bacteriology.

---

What is claimed is:

1. A method of generating nucleic acid fragments, the method comprising:
    contacting a DNA substrate with a polypeptide comprising an amino acid sequence having at least about 90% amino acid sequence identity to the amino acid sequence set forth in any of SEQ ID NOs: 1-22, wherein said contacting comprises contacting a surface comprising a biofilm, wherein the DNA substrate is extracellular DNA from microorganisms present in the biofilm, and wherein the contacting results in generation of nucleic acid fragments.

2. The method of claim 1, wherein said contacting is for about 0.1 hour to 24 hours.

3. The method of claim 1, wherein the polypeptide comprises an amino acid sequence having at least about 95% amino acid identity to the amino acid sequence set forth in any of SEQ ID NOs: 1-22.

4. The method of claim 1, wherein said contacting results in generation of nucleic acid fragments of substantially uniform length.

5. The method of claim 4, wherein the nucleic acid fragments are 60 bp-150 bp in length.

6. A method of generating nucleic acid fragments, the method comprising:
    contacting a DNA substrate with a polypeptide comprising an amino acid sequence having at least about 90% amino acid sequence identity to the amino acid sequence set forth in any of SEQ ID NOs: 1-22, wherein said contacting comprises contacting an epithelial surface of an animal, wherein the DNA substrate is extracellular DNA from microorganisms present on the surface, and wherein the contacting results in generation of nucleic acid fragments.

7. The method of claim 6, wherein the epithelial surface is mucosal membrane.

8. The method of claim 6, wherein the epithelial surface is skin.

9. The method of claim 6, wherein said contacting is for about 0.1 hour to 24 hours.

10. The method of claim 6, wherein the polypeptide comprises an amino acid sequence having at least about 95% amino acid identity to the amino acid sequence set forth in any of SEQ ID NOs: 1-22.

11. The method of claim 6, wherein said contacting results in generation of nucleic acid fragments of substantially uniform length.

12. The method of claim 11, wherein the nucleic acid fragments are 60 bp-150 bp in length.

* * * * *